(12) United States Patent
Stephens et al.

(10) Patent No.: US 11,020,865 B2
(45) Date of Patent: Jun. 1, 2021

(54) SHAVING AID FOR RAZOR CARTRIDGES COMPRISING A NANO-FILAMENT

(71) Applicant: The Gillette Company LLC, Boston, MA (US)

(72) Inventors: Alison Fiona Stephens, Maidenhead (GB); Claire Patricia Humphreys, Southwell (GB); Eduardo Romo Escalante, Reading (GB); Joia Kirin Spooner-Fleming, Jamaican Plain, MA (US); Stephen Robert Glassmeyer, Cincinnati, OH (US); Michael Sean Pratt, Saint Bernard, OH (US); Jonathan Javier Calderas, Cincinnati, OH (US); Min Mao, Deerfield Township, OH (US); Joseph Bryan Edwards, Cambridge, MA (US); Michael John Moloney, Brimfield, MA (US)

(73) Assignee: The Gillette Company LLC, Boston, MA (US)

(*) Notice: Subject to any disclaimer, the term of this patent is extended or adjusted under 35 U.S.C. 154(b) by 299 days.

(21) Appl. No.: 15/632,989

(22) Filed: Jun. 26, 2017

(65) Prior Publication Data

US 2018/0001495 A1  Jan. 4, 2018

Related U.S. Application Data

(60) Provisional application No. 62/357,239, filed on Jun. 30, 2016.

(51) Int. Cl.
*B26B 21/44* (2006.01)
*B26B 21/22* (2006.01)
(Continued)

(52) U.S. Cl.
CPC ............ *B26B 21/443* (2013.01); *A61K 8/027* (2013.01); *A61K 8/31* (2013.01); *A61K 8/342* (2013.01); *A61K 8/8129* (2013.01); *A61K 8/8152* (2013.01); *A61K 8/86* (2013.01); *A61K 8/891* (2013.01); *A61Q 9/02* (2013.01); *B26B 21/222* (2013.01); *B26B 21/4012* (2013.01); *B26B 21/4068* (2013.01); *D01D 5/0007* (2013.01);
(Continued)

(58) Field of Classification Search
CPC .......... Y10T 83/04; A61K 8/027; A61K 8/31; A61K 8/342; A61K 8/8129; A61K 8/8152; A61K 8/86; A61K 8/891; A61K 2800/412; A61Q 9/02; B26B 21/222; B26B 21/4012; B26B 21/4068; D01D 5/0007; D01D 5/426; D04H 3/16
USPC .................................................. 30/537, 538
See application file for complete search history.

(56) References Cited

U.S. PATENT DOCUMENTS

| | | | |
|---|---|---|---|
| 5,454,164 A * | 10/1995 | Yin | B26B 21/443 30/41 |
| 5,958,394 A | 9/1999 | Smith | |
| 9,545,364 B2 | 1/2017 | Glenn, Jr. et al. | |
| 10,045,915 B2 | 8/2018 | Glenn, Jr. et al. | |

(Continued)

FOREIGN PATENT DOCUMENTS

GB  2423494  8/2006

*Primary Examiner* — Phong H Nguyen
(74) *Attorney, Agent, or Firm* — Kevin C. Johnson

(57) ABSTRACT

A shaving aid for razor cartridges comprising water soluble filaments having nano-sized diameters and exhibiting lubricating properties and with improved visual and tactile aesthetics.

15 Claims, 5 Drawing Sheets

(51) Int. Cl.

| | | |
|---|---|---|
| | *B26B 21/40* | (2006.01) |
| | *D01D 5/00* | (2006.01) |
| | *D04H 3/16* | (2006.01) |
| | *D01D 5/42* | (2006.01) |
| | *A61K 8/81* | (2006.01) |
| | *A61K 8/02* | (2006.01) |
| | *A61Q 9/02* | (2006.01) |
| | *A61K 8/31* | (2006.01) |
| | *A61K 8/891* | (2006.01) |
| | *A61K 8/86* | (2006.01) |
| | *A61K 8/34* | (2006.01) |

(52) U.S. Cl.
CPC ............... *D01D 5/426* (2013.01); *D04H 3/16* (2013.01); *A61K 2800/412* (2013.01)

(56) References Cited

U.S. PATENT DOCUMENTS

| | | | |
|---|---|---|---|
| 10,125,336 B2* | 11/2018 | Stephens | C10M 107/34 |
| 2006/0225285 A1 | 10/2006 | Slavtcheff et al. | |
| 2008/0060201 A1 | 3/2008 | Kwiecien | |
| 2011/0177332 A1* | 7/2011 | Park | C08L 71/02 |
| | | | 428/364 |
| 2012/0023763 A1 | 2/2012 | Ariyanayagam et al. | |
| 2012/0094006 A1 | 4/2012 | Kwiecien | |
| 2014/0322153 A1* | 10/2014 | Stephens | A61K 8/86 |
| | | | 424/70.11 |
| 2014/0329428 A1 | 11/2014 | Glenn, Jr. et al. | |
| 2015/0315350 A1 | 11/2015 | Mao et al. | |
| 2016/0047061 A1* | 2/2016 | Huang | D04H 1/4358 |
| | | | 264/468 |
| 2017/0361254 A1* | 12/2017 | Huang | A41D 13/11 |
| 2018/0001494 A1 | 1/2018 | Stephens et al. | |

* cited by examiner

Example 6

Web example 6

Example 6A

Example L6

Example L4

Example L5

SHAVING AID FOR RAZOR CARTRIDGES COMPRISING A NANO-FILAMENT

FIELD OF THE INVENTION

The invention relates to a shaving aid for razor cartridges comprising water soluble filaments based shaving aid exhibiting lubricating properties and with improved visual and tactile aesthetics.

BACKGROUND OF THE INVENTION

The use of shaving aids on razor blades to provide lubrication benefits during the shave is known; see for example U.S. Pat. Nos. 7,121,754, 6,298,558, 5,711,076, 6,301,785, US2009/0223057 and US2006/0225285. Such shaving aids, typically called Lubrastrips, comprise a water-insoluble matrix material to provide structural integrity and a water-soluble polymer, such as polyethylene oxide, in order to provide lubrication during the shave once the water-soluble polymer forms a solution with the water present during shaving. Since the introduction of Lubrastrips, little development has been made in the field, even though these forms are not without limitations. For example, the polyethylene oxide lubricant can be perceived negatively by the consumer due to its inherent stringiness, the form and manufacturing process can degrade the polyethylene oxide efficacy and limit the inclusion of skin care actives and Lubrastrips are a hard non-compliant form that does not provide an appealing sensation on the skin.

Consequently, there is still a need to provide a shaving aid for razor cartridges exhibiting lubricating properties with the ability to contain and deliver a range of desirable skin actives in a controlled manner over multiple usage events, whilst also providing a differentiated and appealing visual and tactile aesthetics before and during use.

Surprisingly, it has been found that the provision of water soluble filaments on a razor cartridge, in a shaving aid for example, can provide these desired benefits. The filaments are preferably comprised of water soluble materials which act as both filament forming materials and lubricants whilst providing a desirable aesthetic before and during use. Optionally, the shaving aid may be coated or impregnated with skin care actives and/or laminated to further increase conformability and the perception of softness. Both the coating or impregnation and lamination also have the additional desired effect of controlling the rate of dissolution of the filaments and associated shaving aid in use.

Fibrous or filament forms are known for use on razor cartridges, as described for example in WO2013/096178. The fibres are described as resilient and non-water soluble and comprise a hydrophobic non-woven material including a polyamide or polyester. The function of the fibres is merely to act as an applicator and reservoir for shaving fluid dispensed into or onto the fibrous pad rather than any for an additional functional benefit. A problem with such resilient fibre or filament pads however is that the pads are prone to forming an undesirable appearance over use due to skin and hair debris collecting in the interstices.

The use of filament or fibrous substrates, often termed as non-woven substrates are described in consumer applications such as tissue towel and are characterized by a desirable cloth like feel and appearance. For example, US2013/0209272 describes a wet wipe comprising a non-woven substrate including polyvinyl alcohol filaments or fibres and a surface treatment of hydrophilic material. Such webs can also be stacked or layered as described in WO20090022761 which describes stacking of dissolvable nano webs comprising fibres or filaments including starch and PVA. However, these webs have a high rate of dissolution and are not suitable for multiple usage. The use of filament forming materials that release actives in use are also described for example in US2012/0052036, US2012/0237576 and US2013/017142.

Very thin fibers have also been disclosed in other publications, see e.g., WO2001026610, WO 2001051690, and U.S. Pat. Nos. 8,367,570 and 7,390,760. Despite these and other disclosures, there remains a need for innovation on the shaving aid space as conventional shaving aids can be limited in the amount or type of lubrication they provide and there can be a need for meaningful skin benefits which have not been offered in other shaving aids on the market.

SUMMARY OF THE INVENTION

The present invention fulfills the need described above by providing nano-diameter sized filaments ("defined herein as nano-filaments") which are water soluble filaments for incorporation onto a razor cartridge for example in or on the housing or in the form of a shaving aid for a razor cartridge. Also within the scope of the present invention is the addition of larger filaments (referred to hereinafter as "filaments") which can also be made of water soluble materials. The shaving aid may employ one or more layers of webs comprising nano-filaments and/or filaments, said webs preferably provide a lubricating benefit, but other skin benefits can also be delivered depending on the components used to form the nano-filaments/filaments. The webs can also be selected and texturized to provide desired visual and tactile aesthetics. Methods of making such nano-filaments are also within the scope of this invention. One embodiment of the invention provides for a method of making a shaving aid comprising: extruding a shaving aid through a die to form an extruded shaving aid, said shaving aid having a skin contacting surface; and electrospinning a nano-filament onto a portion of the skin contacting surface to form a coated shaving aid.

DETAILED DESCRIPTION OF THE INVENTION

Definitions

Figure 1:
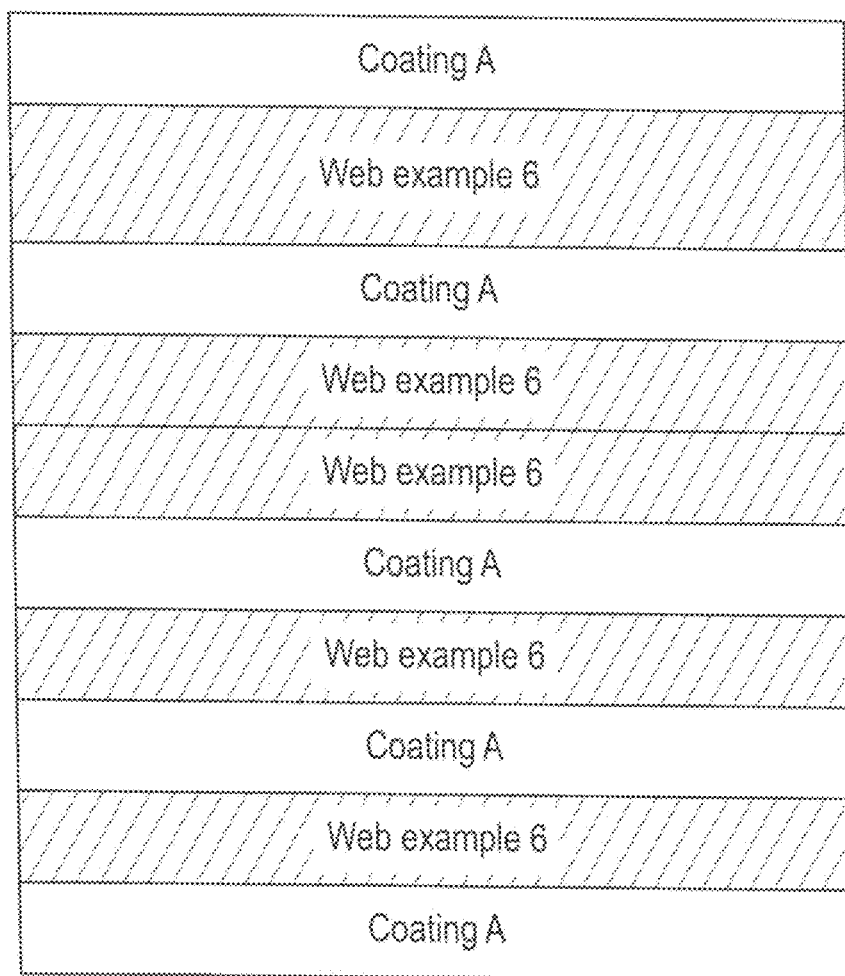
FIGS. 1 to 4 depicts schematic cross sections of webs and laminates examples L1, L2, L3, 6, 6A, L6, L4 and L5 according to the invention.

"Filament" as used herein means an elongate particulate having a length greatly exceeding its diameter, i.e. a length to diameter ratio of at least about 5.

The filaments of the present invention may be spun from filament-forming compositions via suitable spinning processes operations, such as meltblowing, spun bonding and/or electro-spinning.

The filaments of the present invention may be monocomponent and/or multicomponent. For example, the filaments may comprise bicomponent filaments. The bicomponent or multicomponent filaments may be in any form, such as side-by-side, core and sheath, islands-in-the-sea and the like.

The filaments of the present invention may exhibit a length of greater than or equal to 5.08 cm (2 in.) and/or greater than or equal to 7.62 cm (3 in.) and/or greater than or equal to 10.16 cm (4 in.) and/or greater than or equal to 15.24 cm (6 in.). The filament length refers to the length of the filaments after formation. However, in order to utilize the filaments on the razor cartridge or shaving aid therefore, the filaments or webs comprising the filaments may have a length less than the above values.

"Filament-forming composition" as used herein means a composition that is suitable for making a filament of the present invention such as by meltblowing, spunbonding and/or electro-spinning. The filament-forming composition comprises one or more filament-forming materials, preferably a lubricating filament forming material. The filament forming materials exhibit properties that make them suitable for spinning into a filament. In addition to one or more filament-forming materials, the filament-forming composition may optionally comprise one or more additives, for example one or more skin care active agents. In addition, the filament-forming composition may comprise one or more polar solvents, such as water, into which one or more, for example all, of the filament-forming materials and/or one or more, for example all, of the active agents are dissolved and/or dispersed. The total level of filament-forming materials and total level of active agents present in the filament-forming composition may be any suitable amount provided that the filaments of the present invention are produced therefrom.

"Nano-filament" as used herein means a filament having a diameter of less than or equal to 1000 nm. diameter of from about 10 nm to about 1000 nm. The nano-filament comprises a diameter of from about 10 nm to about 1000 nm, preferably from about 250 nm to about 750 nm, about 300 nm to about 600 nm, or even about 350 to about 550 nm. Unless specified otherwise herein, nano-filaments can include the same components as used to form filaments, and any descriptions of measurements regarding filaments can also apply to nano-filaments unless the technique or description is specific to fibers having diameters larger than 1 μm. While the compositional make up of a nano-filament can be the same as a filament, nano-filaments can also be made up of different components and can be made with more specific processing techniques. Those of skill in the art will appreciate that "fibers" and "filaments" can be used interchangeably.

"Filament-forming material" as used herein means a polymer or monomers, preferably water soluble polymers or monomers capable of producing a polymer, which is suitable for making a filament.

"Filament-forming lubricating material" as used herein means a polymer or monomers, preferably water soluble polymer or monomer capable of producing a polymer, that exhibits lubricating properties and which are suitable for making a filament.

"Additive" as used herein means any material present in the filament of the present invention that is not a filament-forming material. An additive may comprise a skin care active agent, a processing aid, a filler, a plasticizer, a cross-linking agent, a rheology modifier, a colourant, a release agent, a chelant and/or an anti-blocking or detackifying agent. An additive comprises any material present in the filament, that if absent from the filament, would not result in the filament losing its filament structure, in other words, its absence does not result in the filament losing its solid form.

"Skin care active agent" as used herein, means an active agent that when applied to the skin provides a benefit or improvement to the skin. The benefit may be immediate or chronic in nature. It includes, but is not limited to cleansing, sebum inhibition, increasing or reducing the oily and/or shiny appearance of skin, reducing dryness and/or redness, itchiness and/or flakiness, reducing skin pore size, exfoliation, desquamation, improving the appearance of the skin tissue, conditioning, moisturizing, smoothening, perfuming, deodorizing skin, reducing inflammation, hair softening, depilatory and/or providing antiperspirant benefits, etc.

"Conditions of intended use" as used herein means the temperature, physical, chemical, and/or mechanical conditions that the filament of the present invention is exposed to when used for its designed purpose of incorporation on a razor cartridge.

"Treatment" as used herein with respect to treating a surface including skin means that the active agent provides a benefit to a surface or environment. Treatments include lubricating the skin, regulating and/or immediately improving the skins cosmetic appearance, cleanliness, smell, and/or feel. In one example treatment in reference to treating skin tissue means deposition of an occlusive skin moisturization agent during the shaving process.

"Weight ratio" as used herein means the weight of filament-forming material (g or %) on a dry weight basis in the filament to the weight of additive, such as active agent(s) (g or %) on a dry weight basis in the filament.

"Hydroxyl polymer" as used herein includes any hydroxyl-containing polymer that can be incorporated into a filament of the present invention, for example as a filament-forming material. The hydroxyl polymer of the present invention comprises greater than 10% and/or greater than 20% and/or greater than 25% by weight hydroxyl moieties.

"Water-soluble material" as used herein means a material that is miscible in water. In other words, a material that is capable of forming a stable (i.e. does not separate for greater than 5 minutes after forming the homogeneous solution) homogeneous solution or dispersion with water at ambient conditions.

"Water-soluble filament" as used herein refers to the water solubility of the filament after completion of the filament forming process and does not include unless specifically stated filaments which have subsequent treatments such as subsequently coating with an additive.

"Ambient conditions" as used herein means 73° F.±4° F. (about 23° C.±2.2° C.) and a relative humidity of 50%±10%.

"Length" as used herein, with respect to a filament, means the length along the longest axis of the filament from one terminus to the other terminus. If a filament has a kink, curl or curves in it, then the length is the length along the entire path of the filament.

"Diameter" as used herein, with respect to a nano-filament or filament, is measured according to the Diameter Test Method described herein. In one example, a filament of the present invention exhibits a diameter of less than 100 μm and/or less than 75 μm and/or less than 50 μm and/or less than 25 μm and/or less than 20 μm and/or less than 15 μm and/or less than 10 μm and/or less than 6 μm and/or greater than 1 μm and/or greater than 3 μm.

"By weight on a dry filament basis" means that the weight of the filament measured immediately after the filament has been conditioned in a conditioned room at a temperature of 73° F.±4° F. (about 23° C.±2.2° C.) and a relative humidity of 50%±10% for 2 hours. In one example, "by weight on a dry filament basis" means that the filament comprises less than 20% and/or less than 15% and/or less than 10% and/or less than 7% and/or less than 5% and/or less than 3% and/or to 0% and/or to greater than 0% based on the weight of the filament of moisture, such as water, for example free water, as measured according to the Water Content Test Method described herein.

"Total level" as used herein, for example with respect to the total level of one or more active agents present in the filament, means the sum of the weights or weight percent of all of the subject materials, for example active agents. In other words, a filament may comprise 25% by weight on a dry filament basis of an anionic surfactant, 15% by weight on a dry filament basis of a nonionic surfactant, 10% by weight of a chelant, and 5% of a perfume so that the total level of active agents present in the filament is greater than 50%; namely 55% by weight on a dry filament basis.

"Web" as used herein means a collection of formed filaments, such as a fibrous structure, and/or a sheet formed of filaments, such as continuous filaments, of any nature or origin associated with one another. In one example, the web is a sheet that is formed via a spinning process, not a cast process.

"Nonwoven web" for purposes of the present invention as used herein and as defined generally by European Disposables and Nonwovens Association (EDANA) means a sheet of filaments, such as continuous filaments, of any nature or origin, that have been formed into a web by any means, and may be bonded together by any means, with the exception of weaving or knitting. Felts obtained by wet milling are not nonwoven webs.

"Particulates" as used herein means granular substances and/or powders.

"Coating" as used herein means the addition of an additive, such as a skin care active agent for example onto at least a portion of the surface of the filaments and/or the web or the voids within the web. The coating may be applied to the individual filaments and/or may be applied onto the web and the voids therein. The coating may be uniform or applied on or into discrete areas of the filament or web. Coating may be applied by any means known in the art such as, but not limited to, spray coating, dip coating, slot coating, printing such as gravure, flexo and inkjet or combinations thereof. The coating may be retained on the surface of the filament of the web to which it is applied or may at least partially impregnate the filaments or web or fill voids within the web.

"Laminate" as used herein is defined as comprising at least two layers of superimposed web, which are bonded together. The layers may be bonded together using for example temperature, pressure and/or the application of water or a thermosetting material, or ultrasound or combinations thereof.

As used herein, the articles "a" and "an" when used herein, for example, "an anionic surfactant" or "a filament" is understood to mean one or more of the material that is claimed or described. All percentages and ratios are calculated by weight unless otherwise indicated. All percentages and ratios are calculated based on the total composition unless otherwise indicated. Unless otherwise noted, all component or composition levels are in reference to the active level of that component or composition, and are exclusive of impurities, for example, residual solvents or by-products, which may be present in commercially available sources.

Filament

The shaving aid or razor cartridge housing of the present invention comprises filaments wherein at least 15%, or at least 30%, or at least 40% or at least 50% or at least 60% or at least 70% or at least 80% or at least 90% by weight of total filament are water soluble filaments. The water-soluble filaments of the present invention preferably comprise one or more filament-forming materials which may comprise one or more filament-forming lubricating materials. The filament forming materials are preferably water-soluble. The shaving aid or razor cartridge housing may optionally further independently comprise 85% or less, 70% or less, or 60% or less, or 50% or less or 40% or less, or 30% or less, or 20% or less or 10% or less or 5% or less by weight of the total filaments of one or more non-water soluble filaments and or non-water soluble filament forming materials and or water. The water-soluble filaments may optionally also further comprise water and or one or more additives and may include one or more skin care active agents.

The filament of the present invention preferably comprises 0% to less than 20%, even more preferably 0% to less than 15%, even more preferably still 2% to less than 10% by weight of water as measured according to the Water Content Test Method described herein.

In one embodiment, the filament may comprise one or more water soluble filament-forming lubricating materials. In another embodiment the filament may comprise one or more additives.

In another embodiment the filament may comprise one or more skin care active agents selected from the group consisting of: surfactants, fats, oils, waxes, quaternary ammonium polymers, humectants, occlusive agent, cationic polymers, sensates, chronic skin care actives, perfume and anti-perspirant actives. In another embodiment, the water-soluble filament comprises a total level of additives of from about 0% to about 70% and a total level of skin care active agents of from about 0% to about 70%. In another embodiment the skin care active agents may be present from about 1% to about 15% by weight of the water soluble filament and or filaments.

The filament may comprise two or more different skin care active agents. The two or more different skin care active agents, may be compatible or incompatible with one another. The filament may comprise an active agent within the filament and an active agent on at least a portion of an external surface of the filament, such as a coating on the filament. The active agent on the external surface of the filament may be the same or different from the active agent present in the filament. If different, the active agents may be compatible or incompatible with one another. Filaments comprising different skin care active agents are also envisaged.

The one or more skin care active agents may be uniformly distributed or substantially uniformly distributed throughout the filament or may be distributed as discrete regions within the filament. The skin active agents described hereinafter may also be used as a coating as described hereinafter.

The filaments of the present invention may be meltblown, spun bond or electrospun filaments. In the case of meltblown or spunbond filaments preferably the filament exhibits a diameter of less than 100 μm, more preferably less than 50 μm, even more preferably less than 25 μm, even more preferably still and/or less than 10 as measured according to the Diameter Test Method described herein. In the case of electrospun filaments, the filament of the present invention preferably exhibits a diameter of less than 1 μm as measured according to the Diameter Test Method described herein. The diameter of a filament of the present invention may be used to control the dissolution rate of the filament and delivery of the water-soluble lubricating materials and/or skin care active agents under the conditions of use.

The filaments are intended for use on a hair removal head, such as a razor cartridge, and may be incorporated as is, attached onto another element of the hair removal head such as the housing of a razor cartridge or shaving aid and/or be used to form a discrete article such as a shaving aid for use on the hair removal head or cartridge.

Filament-Forming Material

The filament-forming material is any suitable material, such as a polymer or monomers capable of producing a polymer that exhibits properties suitable for making a filament, such as by a spinning process. The filament forming material preferably comprises at least 15%, preferably at least 30%, more preferably at least 50% by weight of a water-soluble filament forming material. The filament forming material may comprise up to about 70% by weight, preferably less than 50%, more preferably less than 25%, even more preferably less than 10% by weight of a non-water soluble filament forming material and or additive.

In one embodiment the filament forming material comprises at least one lubricating filament-forming material(s) preferably water soluble lubricating filament forming materials selected from the group consisting of: polymers derived from acrylic monomers such as the ethylenically unsaturated carboxylic monomers and ethylenically unsaturated monomers, polyvinyl alcohol, polyacrylates, polymethacrylates, copolymers of acrylic acid and methyl acrylate, polyvinylpyrrolidones, polyethylene oxide, polyethylene glycol, polpolyacrylamides, starch and starch derivatives, natural or synthetic gums pullulan, gelatin, hydroxypropylmethylcelluloses, methycelluloses, quaternary ammonium polymers and carboxymethycelluloses. Preferably the materials may be selected from a nonionic polymer for example polyethyleneglycol and or polyethyleneoxide, a hydroxyl polymer, such as a polyvinyl alcohol ("PVOH" or "PVA") and/or a quaternary ammonium polymer, or combinations thereof.

a. Water-Soluble Hydroxyl Polymers

Non-limiting examples of water-soluble hydroxyl polymers in accordance with the present invention include polyols, such as polyvinyl alcohol, polyvinyl alcohol derivatives, polyvinyl alcohol copolymers, starch, starch derivatives, starch copolymers, chitosan, chitosan derivatives, chitosan copolymers, cellulose derivatives such as cellulose ether and ester derivatives, cellulose copolymers, hemicellulose, hemicellulose derivatives, hemicellulose copolymers, gums, arabinans, galactans, proteins and various other polysaccharides and mixtures thereof.

Polyvinyl alcohols herein can be grafted with other monomers to modify its properties. A wide range of monomers has been successfully grafted to polyvinyl alcohol. Non-limiting examples of such monomers include vinyl acetate, styrene, acrylamide, acrylic acid, 2-hydroxyethyl methacrylate, acrylonitrile, 1,3-butadiene, methyl methacrylate, methacrylic acid, maleic acid, itaconic acid, sodium vinylsulfonate, sodium allylsulfonate, sodium methylallyl sulfonate, sodium phenylallylether sulfonate, sodium phenylmethallylether sulfonate, 2-acrylamido-methyl propane sulfonic acid (AMPs), vinylidene chloride, vinyl chloride, vinyl amine and a variety of acrylate esters.

In one example, the water-soluble hydroxyl polymer is selected from the group consisting of: polyvinyl alcohols, hydroxymethylcelluloses, hydroxyethylcelluloses, hydroxypropylmethylcelluloses and mixtures thereof. A non-limiting example of a suitable polyvinyl alcohol includes those commercially available from Kuraray (Japan) under the POVAL® tradename, preferably KL318 and/or 420H grades.

b. Non-Ionic Polymer

Examples of suitable non-ionic water soluble polymers suitable for use hererin include polyethylene oxide, polyvinyl pyrrolidone, polyacrylamide, polyvinyl imidazoline, polyethylene glycol, and mixtures thereof. In some embodiments, said water soluble polymer is selected from the group consisting of polyethylene oxide and polyethylene glycol, and mixtures thereof.

One group of preferred water soluble polymers are the polyethylene oxides generally known as POLYOX® (available from Dow Chemicals) or ALKOX® (available from Meisei Chemical Works, Kyoto, Japan). The polyethylene oxides, may have average molecular weights of at least about 20,000, preferably at least about 50,000, preferably at least about 100,000 or from about 100,000 to about 8 million, more preferably about 300,000 to about 5 million.

Another group of preferred water soluble polymers are polyethylene glycols generally known as PEGs and available as CARBOWAX® (from Dow Chemicals) and PLURIOL® (from BASF). The polyethylene glycols may have an average molecular weight of from about 200 to about 8,000, preferably from about 200 to about 600, even more preferably from about 350 to about 450.

In some embodiments it may be advantageous to combine polyethylene oxides with polyethylene glycols.

c. Quaternary Ammonium Polymers

Suitable water soluble cationic polymers are, for example, cationic cellulose derivatives, for example a quaternized hydroxymethyl cellulose obtainable under the name UCARE'® Polymer JR 400 from Dow, hydrophobized quaternized hydroxymethyl cellulose, for example SOFTCAT® SL-5 from Dow, cationic starches, copolymers of diallylammonium salts and acrylamides, copolymers of diallylammonium salts and acrylic acid (Merquat 280 from Lubrizol), quaternized vinylpyrrolidone/vinyl imidazole polymers, for example LUVIQAT® (BASF), condensation products of polyglycols and amines, quaternized collagen polypeptides, for example lauryldimonium hydroxypropyl hydrolyzed collagen (LAMEQUAT® L/Grünau), quaternized wheat polypeptides, polyethyleneimine, cationic silicone polymers, for example amidomethicones, copolymers of adipic acid and Dimethyl-aminohydroxypropyldiethylene-triamine (CARTARETIN®/Clariant), copolymers of acrylic acid with dimethyldiallylammonium chloride (MERQUAT® 550/Chemviron), polyaminopolyamides, as described, for example, in FR-A-2 252840, and the cross-linked water-soluble polymers thereof, cationic chitin derivatives, for example of quaternized chitosan, optionally distributed as microcrystals; condensation products of dihaloalkyls, for example dibromobutane, with bisdialkylamines, for example bisdimethylamino-1,3-propane, cationic guar gum, for example JAGUAR® C-17 from Celanese or N-HANCE® 3196 from Ashland, quaternized ammonium salt polymers, for example MIRAPOL® A-15, MIRAPOL® AD-1, MIRAPOL® AZ-1 from Miranol, ampholytic terpolymers comprised of methacrylamidopropyl trimethyl ammonium chloride, acrylamide and acrylic acid, for example Merquat 2003PR.

In one embodiment the filament forming material is selected from polyvinyl alcohol, polyethylene oxide, polyethylene glycol and mixtures thereof. In other embodiment, the filament forming material is selected from polyethylene oxide. In other example the filament forming material is selected from a quaternary ammonium polymer, preferably a copolymer of a diallylammonium salt and acrylic acid.

Nano-Filaments

As explained above, nano-filaments can be made up of the same polymers, monomers, or mixtures thereof as described above with regards to filaments. In one embodiment, the invention comprises a shaving aid comprising at least one nano-filament. In one embodiment, the invention comprises a shaving aid comprising a second nano-filament. In one embodiment, the invention comprises a shaving aid comprising a mixture of two or more different nano-filaments. In one embodiment, the invention comprises a shaving aid comprising a filament and a nano-filament.

In one embodiment, the nano-filament consists essentially of one or more water soluble polymers. Suitable polymers for forming the nano-filament include polyvinyl alcohol, quaternary ammonium polymer, polyethylene glycol, polyethyleneoxide, polypropylene oxide, or a combination thereof. In one embodiment, the nano-filament is a copolymer of polyethylene oxide and polypropylene oxide, such as those disclosed in U.S. Pat. No. 5,454,164, EP2988831A and EP2988832A.

In one embodiment, the nano-filaments are cross linked. One way to cross link the nano-filaments is to use a modified water soluble polymer such as a modified PEO. In one embodiment, the PEO has been modified to prevent its dissolution in water. Without intending to be bound by theory, it is believed that when nanofibers based on water-soluble polymers are crosslinked, they only swell in an aqueous solution and form hydrogels. This has been explained in Zhou et al, UV-initiated crosslinking of electrospun poly(ethylene oxide) nanofibers with pentaerythritol triacrylate: Effect of irradiation time and incorporated cellulose nanocrystals. Carbohydrate Polymers 87 (2012) 1779-1786. Specific crosslinking mechanisms can include treatment by UV irradiation. In such a situation the PETA could form an excited triplet state, and then absorb a proton from PEO chain and cleave C=O bond of PETA to form a PEO radical and a PETA radical, respectively. PEO radical produced attacks the C=C bond of PETA to initiate the polymerization of PETA. These obtained chains are terminated through radical coupling to form the crosslinking between PEO and PETA.

In another embodiment, the nano-filament also comprise non-water soluble components. In one embodiment, the nano-filament has a water-soluble sheath surrounding a non-soluble core, referred to herein as a co-axial nano-filament. In one embodiment, the co-axial nano-filament comprises at least two components, wherein said two components are immiscible. The core can be in liquid or solid form. The core can comprise a non-soluble material. The core can also comprise a hydrophobic material. Preferably, the core comprises a skin care active. One type of co-axial nano-filament for use with the present invention comprises PEO sheath formed around a liquid polydimethylsiloxane silicone core (PMX-200 by Dow Corning at 200 cSt viscosity). In one embodiment the core has a diameter of from about 90 nm to about 900 nm. In one embodiment, the sheath has a diameter of from about 100 nm to 1000 nm. In one embodiment, the co-axial nano-filament has more than one sheath surrounding the core. One embodiment of the present invention provides for a method of making a shaving aid comprising a co-axial nano-filament. One way to make such a filament is to use a specialty coaxial emitter tip and an extra syringe pump to drive two fluids concentrically inside one another into the charged field used to electrospin the nano-filament. The electrospinning process forms fibers from those two starting fluids while maintaining their concentric geometry.

In one embodiment the nano-filament has a diameter of from about 10 nm to about 1000 nm, preferably from about 250 nm to about 750 nm, about 300 nm to about 600 nm, or even about 350 to about 550 nm. Those of ordinary skill in the art will understand that the average diameter can be calculated using an imaging analysis technique. One suitable imaging analysis technique is to use a field emission scanning electron microscopy (FESEM). One way to do this is to sputter coat the fiber substrate or web with an electrically conductive metal (such as gold, platinum, silver, chromium, or iridium) and then examine the filaments using FESEM. Specifically in one embodiment, gold is sputter coated onto the fiber sample for 30 seconds prior to FESEM imaging. Imaging is then performed with a Hitachi S-4200 FESEM and filament diameter measurements are collected using ImageJ to analyze the SEM images. In one embodiment at least one filament in the shaving aid is a nano-filament. In another embodiment where a plurality of filaments are present having a diameter less than 1000 nm, the average diameter of such nano-filaments can be from about 300 nm to about 600 nm, preferably from about 350 nm to about 550 nm.

Skin Care Active Agents

In one embodiment the filament, web or shaving aid may comprise a "Skin care active agent". Non-limiting examples of suitable cosmetic agents, skin care agents and, skin conditioning agents, are described in CTFA Cosmetic Ingredient Handbook, Second Edition, The Cosmetic, Toiletries, and Fragrance Association, Inc. 1988, 1992 and include fats, oils, waxes, surfactants, perfumes, humectants, quaternary polymers, cooling agents and mixtures thereof. In one embodiment, the skin care active agents are hydrophobic. The skin care active agents may be utilized to provide both immediate and single application benefits and or to address chronic skin conditions requiring multiple applications. The skin care active agents may be present within the filament, on a portion of the external surface thereof or may be applied as a coating on the formed web as discussed hereinafter.

i. Fats, Oils and Waxes

Suitable oils may be selected from natural oil, synthetic oil, silicone oil and mixtures thereof. Non-limiting examples of suitable natural oils include Acetylated Castor Oil, Acetylated Hydrogenated Castor Oil, *Actinidia Chinensis* (Kiwi), Seed Oil, *Adansonia Digitata* Oil, *Aleurites Moluccana* Seed Oil, *Anacardium Occidentale* (Cashew) Seed Oil, *Arachis Hypogaea* (Peanut) Oil, *Arctium Lappa* Seed Oil, *Argania Spinosa* Kernel Oil, *Argemone Mexicana* Oil, *Avena Sativa* (Oat) Kernel Oil, *Bertholletia Excelsa* Seed Oil, *Borago Officinalis* Seed Oil, *Brassica Campestris* (Rapeseed) Seed Oil, *Calophyllum Tacamahaca* Seed Oil, *Camellia Japonica* Seed Oil, *Camellia Kissi* Seed Oil, *Camellia Oleifera* Seed Oil, Canola Oil, Caprylic/Capric/ Lauric Triglyceride, Caprylic/Capric/Linoleic Triglyceride, Caprylic/Capric/My-ristic/Stearic Triglyceride, Caprylic/ Capric/Stearic Triglyceride, Caprylic/Capric Triglyceride, Carthamus Tinctorius (Hybrid Safflower) Seed Oil, Carthamus Tinctorius (Safflower) Seed Oil, *Carum Carvi* (Caraway) Seed Oil, *Carya* Illinoensis (Pecan) Seed Oil, Castor Oil Benzoate, *Chenopodium Quinoa* Seed Oil, *Cibotium Barometz* Oil, *Citrullus* Vulgaris (Watermelon) Seed Oil, *Cocos Nucifera* (Coconut) Oil, *Coffea Arabica* (Coffee) Seed Oil, *Coix Lacryma-Jobi* (Job's Tears) Seed Oil, *Corylus Americana* (Hazel) Seed Oil, *Corylus Avellana* (Hazel) Seed Oil, *Cucumis Sativus* (Cucumber) Oil, *Cucurbita Pepo* (Pumpkin) Seed Oil, *Daucus Carota Sativa* (Carrot) Seed Oil, *Elaeis Guineensis* (Palm) Kernel Oil, *Elaeis Guineensis* (Palm) Oil, *Gossypium* (Cotton) Seed Oil, *Helianthus Annuus* (Hybrid Sunflower) Oil, *Helianthus Annuus* (Sunflower) Seed Oil, *Hippophae Rhamnoides* Oil, Human *Placental Lipids*, Hydrogenated Canola Oil, Hydrogenated Castor Oil, Hydrogenated Castor Oil Laurate, Hydrogenated Castor Oil Triisostearate, Hydrogenated Coconut Oil, Hydrogenated Cottonseed Oil, Hydrogenated C12-18 Triglycerides, Hydrogenated Fish Oil, Hydrogenated Lard, Hydrogenated *Menhaden* Oil, Hydrogenated Olive Oil, Hydrogenated Orange Roughy Oil, Hydrogenated Palm Kernel Oil, Hydrogenated Palm Oil, Hydrogenated Peanut Oil, Hydrogenated Rapeseed Oil, Hydrogenated Shark Liver Oil, Hydrogenated Soybean Oil, Hydrogenated Sunflower Seed Oil, Hydrogenated Tallow, Hydrogenated Vegetable Oil, *Isatis Tinctoria* Seed Oil, *Juglans Regia* (Walnut) Seed Oil, Lauric/Palmitic/Oleic Triglyceride, *Umnanthes Alba* (Meadowfoam) Seed Oil, Unum *Usitatissimum* (Linseed) Seed Oil, *Lupinus Albus* Seed Oil, *Macadamia Integrifolia* Seed Oil, *Macadamia Ternifolia* Seed Oil, *Maleated Soybean* Oil, *Mangifera Indica* (Mango) Seed Oil, *Marmot* Oil, *Melaleuca Alternifolia* (Tea Tree) Leaf Oil, *Melia Azadirachta* Seed Oil, *Melissa Officina lis* (Balm Mint) Seed Oil, *Menhaden* Oil, *Moringa pterygosperma* Seed Oil, *Mortierella* Oil, *Neatsfoot* Oil, *Nelumbium Speciosum* Flower Oil, *Nigella Sativa* Seed Oil, *Oenothera Biennis* (Evening Primrose) Oil, *Olea Europaea* (Olive) Fruit Oil, *Olea Europaea* (Olive) Husk Oil, Orange Roughy Oil, *Orbignya Cohune* Seed Oil, *Orbignya Oleifera* Seed Oil, *Oryza Sativa* (Rice) Bran Oil, *Oryza Sativa* (Rice) Germ Oil, *Ostrich* Oil, *Oxidized* Corn Oil, *Oxidized* Hazel Seed Oil, *Papaver Orientale* (Poppy) Seed Oil, *Passiflora Edulis* Seed Oil, *Persea Gratissima* (Avocado) Oil, *Pistacia Vera* Seed Oil, *Placental Lipids, Prunus Amygdalus Amara* (Bitter Almond) Kernel Oil, *Prunus Amygdalus Dulcis* (Sweet Almond) Oil, *Prunus Armeniaca* (Apricot) Kernel Oil, *Prunus Avium* (Sweet Cherry) Seed Oil, *Prunus Cerasus* (Bitter Cherry) Seed Oil, *Prunus Persica* (Peach) Kernel Oil, *Pyrus Malus* (Apple) Oil, *Ribes Nigrum* (Black Currant) Seed Oil, *Ricinus Communis* (Castor) Seed Oil, *Rosa Canina* Fruit Oil, *Rosa Moschata* Seed Oil, *Salvia Hispanica* Seed Oil, *Santalum Album* (Sandalwood) Seed Oil, *Sesamum Indicum* (Sesame) Seed Oil, *Solanum Lycopersicum* (Tomato) Seed Oil, Soybean Lipid, *Sphingolipids, Taraktogenos Kurzii* Seed Oil, *Telphairia Pedata* Oil, Vegetable Oil, *Vitis Vinifera* (Grape) Seed Oil, *Zea Mays* (Corn) Germ Oil, *Zea Mays* (Corn) Oil, mineral oil and mixtures thereof.

Suitable synthetic oils include hydrocarbons, esters, alkanes, alkenes and mixtures thereof. Non-limiting examples include isopropyl palmitate, isopropyl stearate, isohexadecane, isododecane, polyglyceryl triisostearate and mixtures thereof.

Non-limiting examples of suitable silicone oils include dimethicones (including partial esters of dimethicones and fatty acids derived from natural/synthetic oils), cyclomethicones, phenylated silicones, phenyl trimethicones, trimethyl pentaphenyl trisiloxane and mixtures thereof.

Non-limiting examples of commercially available silicone oils include Dow Corning 200 fluid, Dow Corning 244, Dow Corning 245, Dow Corning 344, and Dow Corning 345, (commercially available from Dow Corning Corp.); SF-1204 and SF-1202 Silicone Fluids (commercially available from G.E. Silicones), GE 7207 and 7158 (commercially available from General Electric Co.); and SWS-03314 (commercially available from SWS Silicones Corp.), the Viscasil series (sold by General Electric Company), SF 1075 methylphenyl fluid (sold by General Electric Company) and 556 Cosmetic Grade Fluid (sold by Dow Corning Corp.), Silshine 151 (sold by Momentive), PH1555 and PH1560 (sold by Dow Corning) and Silwets such as Silwets 7210, 7230 and 7220 (available from by Momentive).

Suitable triglycerides, may have the following formula:

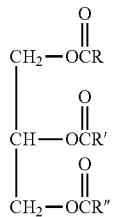

wherein R, R' and R" may be the same as or different from one or both of the others, wherein each of R, R' and R" is a fatty acid and wherein the or each triglyceride is solid at 25° C.

Suitable oils from which triglycerides may be formed from include, but are not limited to, the oils listed herein. Suitable fatty acids for formation of triglycerides include, but are not limited to, Myristoleic acid, Palmitoleic acid, Sapienic acid, Oleic acid, Linoleic acid, α-Linolenic acid, Arachidonic acid, Eicosapentaenoic acid, Docosahexaenoic acid, Lauric acid ($C_{12}$), Myristic acid ($C_{14}$), Palmitic acid ($C_{16}$), Stearic acid ($C_{18}$), Arachidic acid ($C_{20}$) and mixtures thereof.

Specific sources of triglycerides suitable for inclusion herein include Shea Butter, *Theobroma Cacao* (Cocoa) Seed Butter, Cocoa Butter, *Mangifera Indica* (Mango) Seed Butter, Kokum Butter and mixtures thereof. Particularly preferred are shea butter, cocoa butter and mixtures thereof.

The wax may comprise natural wax, synthetic wax or mixtures thereof. Natural waxes may be plant, animal or mineral derived. Non-limiting examples of suitable natural waxes include Beeswax, *Copernicia Cerifera* (Carnauba) Wax, *Euphorbia Cerifera* (Candelilla) Wax, Jojoba Wax, *Oryza Sativa* (Rice) Bran Wax, Lemon peel wax, Soybean wax, Sunflower wax and mixtures thereof.

Non-limiting examples of suitable synthetic waxes include Hydrogenated Jojoba Wax, synthetic and siliconyl jojoba wax, Hydrogenated Microcrystalline Wax, Microcrystalline Wax, synthetic, siliconyl and Hydrogenated Rice Bran Wax, Ceresin, Ozokerite, Paraffin, benhenyl beeswax, synthetic, siliconyl and hydrogenated Beeswax, synthetic, hydrogenated and siliconyl Candelilla Wax, Synthetic, hydrogenated and siliconyl Carnauba wax, synthetic, hydrogenated and siliconyl lemon peel wax, synthetic, siliconyl and hydrogenated soybean wax, synthetic, siliconyl and hydrogenated sunflower wax and mixtures thereof. Preferred natural and synthetic waxes are Beeswax, Microcrystalline wax, Candellila wax, Ozokerite, and mixtures thereof.

Non-limiting examples of suitable silicone waxes include, Stearyoxy trimethylsilane such as DC580 wax, C30-45 alkyl methicone available as DC AMS-C30 Cosmetic Wax, stearyoxymethyl silane available as DC Silkywax 10, C24-54 alkyl methicone such as DC ST-Wax 30, C30-45 Alkyldimethylsilyl, Polypropyl-silsesquioxane, available as DC SW-8005 resin wax, and mixtures thereof.

Particularly preferred oils, waxes or fats suitable as skin care active agents are selected from PDMS silicone fluids, mineral oil, and petrolatum, naturally derived oils such as olive oil derivatives or mixtures thereof. In one example, fats, oils and/or waxes are present in ranges from about 0.01% to about 60% w/w on a dry weight basis of the water-soluble filament, preferably from about 1% to about 40%, more preferably from about 5% to about 30% by weight of the water-soluble filament.

In another example, the amount of fats, oils and/or waxes may be present as a coating on the filaments or formed web.

In such embodiments, the fats, oils and/or waxes may be e present in weight ratios of about 4:1 (web: fats, oils and/or waxes) to about 1:8 (web: fats, oils and/or waxes). In such embodiments the fats, oils and/or waxes may be present in or on the surface of the individual filaments and or applied as a coating to formed web as discussed hereinafter.

ii. Surfactants

Non-limiting examples of suitable surfactants include anionic surfactants, cationic surfactants, nonionic surfactants, zwitterionic surfactants, amphoteric surfactants, and mixtures thereof.

a. Anionic Surfactants

Non-limiting examples of suitable anionic surfactants include alkyl sulfates, alkyl ether sulfates, branched alkyl sulfates, branched alkyl alkoxylates, branched alkyl alkoxylate sulfates, mid-chain branched alkyl aryl sulfonates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, sodium lauroyl glutamate, and combinations thereof.

Alkyl sulfates and alkyl ether sulfates suitable for use herein include materials with the respective formula $ROSO_3M$ and $RO(C_2H_4O)_xSO_3M$, wherein R is alkyl or alkenyl of from about 8 to about 24 carbon atoms, x is 1 to 10, and M is a water-soluble cation such as ammonium, sodium, potassium and triethanolamine Other suitable anionic surfactants are described in McCutcheon's Detergents and Emulsifiers, North American Edition (1986), Allured Publishing Corp. and McCutcheon's, Functional Materials, North American Edition (1992), Allured Publishing Corp.

b. Nonionic Surfactants

Non-limiting examples of non-ionic surfactants are copolymers of polyethylene oxide (PEO) and polypropylene oxide (PPO) and copolymers of polysorbate and a fatty acid. Commercially these materials are available under the tradenames of PLURONICS® and TWEENs' respectively.

The PEO/PPO copolymer may have any average molecular weight. Advantageously, the PEO/PPO copolymer has an average molecular weight of at least 5,000, preferably in the range of from 10,000 to 20,000, more preferably from 11,000 to 15,000, even more preferably from 12,000 to 13,000 and even more preferably still from 12,250 to 12,750. Without wishing to be bound by theory, the inclusion of a PEO/PPO copolymer of sufficient molecular weight is thought to further improve the lubrication properties of the water-soluble polymer in aqueous solution, especially for polyethylene oxide, and thus prevent an undesirable feeling in use.

The PEO/PPO copolymer may be of any arrangement but is advantageously a block copolymer, for example a di-block, tri-block, multi-block, radial-block or random-block copolymer. Preferably, the PEO/PPO copolymer is a tri-block copolymer, more preferably a tri-block copolymer having the sequence: PEO-PPO-PEO. Such tri-block copolymers of PEO and PPO are commercially available under tradenames such as PLURACARE® from BASF and PLURONIC® from Sigma-Aldrich.

TWEENs are ethoxylated esters formed by esterification of sorbitol with a fatty acid. Both the degree of ethoxylation and esterification can be modified as can the length of the fatty acid alkyl chain. For example, the fatty acid chain can range from lauric acid (C12) to stearic (C18) and oleic (C18:1) acid. Ethoxylation can vary from 4 to 20 units. Increasing the degree of ethoxylation and decreasing the molecular weight of the fatty acid chain both increase the aqueous solubility of the material and so increase the HLB. Preferably TWEENS are selected in which hydrophilic behavior dominates, these are typically TWEENs with an HLB of 11 or above. Preferably the HLB is at least 11, even more preferably it is above 13 and most preferred are an HLB of above 15.

The concentration of non-ionic surfactants typically ranges from about 0.01% to about 15% w/w on a dry weight basis of the filament or of the web.

c. Zwitterionic Surfactants

Non-limiting examples of zwitterionic or ampholytic surfactants include: derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 at column 19, line 38 through column 22, line 48, for examples of zwitterionic surfactants; betaines, including alkyl dimethyl betaine and cocodimethyl amidopropyl betaine, $C_8$ to $C_{18}$ (for example from $C_{12}$ to $C_{18}$) amine oxides and sulfo and hydroxy betaines, such as N-alkyl-N, N-dimethylammino-1-propane sulfonate where the alkyl group can be $C_8$ to $C_{18}$ and in certain embodiments from $C_{10}$ to $C_{14}$.

iii. Perfumes

One or more perfume and/or perfume raw materials such as accords and/or notes or perfumery ingredients may be incorporated into one or more of the filaments or web or shaving aid of the present invention. The perfume may comprise a perfume ingredient selected from the group consisting of: aldehyde perfume ingredients, ketone perfume ingredients, and mixtures thereof.

A wide variety of natural and synthetic chemical ingredients useful as perfumes and/or perfumery ingredients include but not limited to aldehydes, ketones, esters, and mixtures thereof. Also included are various natural extracts and essences which can comprise complex mixtures of ingredients, such as orange oil, lemon oil, rose extract, lavender, musk, patchouli, balsamic essence, sandalwood oil, pine oil, cedar, and the like. Finished perfumes can comprise extremely complex mixtures of such ingredients. Typically a finished perfume comprises from about 0.01% to about 2%, by weight on a dry filament basis dry web basis or as a % w/w of the shaving aid.

The perfume may be included as the raw material or included in a perfume delivery system, including but not limited to a cyclodextrin, a frangible micro-sphere, an inorganic carrier material or a starch encapsulated accord or mixture thereof.

iv. Quaternary Ammonium Polymers

The filaments, webs and shaving aids of the present invention may additionally further comprise a cationic polymer as a skin conditioning agent. Such polymers may also be utilized as filament forming materials but may further be added to the formed filaments or web as a coating to deliver further skin conditioning benefits. Concentrations of the cationic polymer in the filaments when present as a coating, typically range from about 0.05% to about 3% and/or from about 0.075% to about 2.0% and/or from about 0.1% to about 1.0% by weight on a dry filament basis. Alternatively, the coating composition may comprise a quaternary ammonium polymer and is preferably present from 0% to 20% w/w, more preferably from 0% to 10% w/w, of the filament, web and or shaving aid.

Non-limiting examples of suitable cationic polymers may have cationic charge densities of at least 0.5 meq/gm and/or at least 0.9 meq/gm and/or at least 1.2 meq/gm and/or at least 1.5 meq/gm at a pH of from about 3 to about 9 and/or from about 4 to about 8. In one example, cationic polymers suitable as conditioning agents may have cationic charge densities of less than 7 meq/gm and/or less than 5 meq/gm at a pH of from about 3 to about 9 and/or from about 4 to about 8. Herein, "cationic charge density" of a polymer refers to the ratio of the number of positive charges on the polymer to the molecular weight of the polymer. The weight average molecular weight of such suitable cationic polymers will generally be between about 10,000 and 10 million, in one embodiment between about 50,000 and about 5 million, and in another embodiment between about 100,000 and about 3 million.

Suitable cationic polymers for use herein may contain cationic nitrogen-containing moieties such as quaternary ammonium and/or cationic protonated amino moieties. Any anionic counterions may be used in association with the cationic polymers so long as the cationic polymers remain soluble in water and so long as the counterions are physically and chemically compatible with the other components of the filaments or do not otherwise unduly impair product performance, stability or aesthetics of the filaments. Non-limiting examples of such counterions include halides (e.g., chloride, fluoride, bromide, iodide), sulfates and methylsulfates. Non-limiting examples of such cationic polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

Other suitable cationic polymers for use in the filaments, webs or shaving aid of the present invention include cationic polysaccharide polymers, cationic guar gum derivatives, quaternary nitrogen-containing cellulose ethers, cationic synthetic polymers, cationic copolymers of etherified cellulose, guar and starch. When used, the cationic polymers herein are soluble in water. Further, suitable cationic polymers for use in the filaments of the present invention are described in U.S. Pat. Nos. 3,962,418, 3,958,581, and U.S. 2007/0207109A1, which are all incorporated herein by reference.

The concentration of the conditioning agents in the filaments, webs and or shaving aid may be sufficient to provide the desired conditioning benefits. Such concentration can vary with the conditioning agent, the conditioning performance desired, the average size of the conditioning agent particles, the type and concentration of other components, and other like factors and may be selected accordingly.

v. Humectants

The filaments, webs or shaving aids of the present invention may contain one or more humectants. The humectants herein are selected from the group consisting of polyhydric alcohols, water soluble alkoxylated nonionic polymers, and mixtures thereof.

vi. Coolant Compounds

The filaments, webs or shaving aids of the present invention may contain one or more coolant compounds. A large number of coolant compounds of natural or synthetic origin are known. Among natural coolants, peppermint oil, camphor, *eucalyptus* oil, thymol and lavender oil are the most common. Among synthetic coolants, many are derivatives of or are structurally related to menthol, i.e., containing the cyclohexane moiety, and derivatized with functional groups including carboxamide, ketal, ester, ether and alcohol. Non-limiting examples include methyl methylamido oxalate, (under the tradename FRESCOLAT® X-cool available from Symrise), menthyl lactate (such as Frescolate ML Natural available from Symrise), and Menthyl Pyrrolidone Carboxylate also known as Menthyl PCA (under the tradename QUESTICES® available from Givaudan).

vii. Color Agents

The filaments, webs or shaving aids of the present invention may comprise one or more color agents or colorants. The color agents may be used in amounts effective to produce a desired color. The color agents useful in the present invention include pigments such as titanium dioxide and/or iron oxides, mica based pigments, natural food colors and dyes suitable for food, drug and cosmetic applications, and mixtures thereof.

Additional Additives i. Suspending Agents

The filaments of the present invention may further comprise a suspending agent at concentrations effective for suspending water-insoluble material in dispersed form in the compositions or for modifying the viscosity of the filament forming composition. Such concentrations of suspending agents range from about 0.1% to about 10% and/or from about 0.3% to about 5.0% by weight on a dry filament basis.

Non-limiting examples of suitable suspending agents include anionic polymers and nonionic polymers (e.g., vinyl polymers, acyl derivatives, long chain amine oxides, and mixtures thereof, alkanol amides of fatty acids, long chain esters of long chain alkanol amides, glyceryl esters, primary amines having a fatty alkyl moiety having at least about 16 carbon atoms, secondary amines having two fatty alkyl moieties each having at least about 12 carbon atoms). Examples of suspending agents are described in U.S. Pat. No. 4,741,855.

ii. Other Additives

The filament and/or web of the present invention can include one or more excipients. Non-limiting examples of excipients can include non-water soluble filament-forming materials or non-water soluble filaments, aesthetic agents, chelants, preservatives, UV absorbers, solid or other liquid fillers, colliodal silica, probiotics, deposition aids, BHT, pearlescent agents, effervescent agents, color change systems, opacifiers, vitamins and amino acids such as: water soluble vitamins and their derivatives, water soluble amino acids and their salts and/or derivatives, water insoluble amino acids, viscosity modifiers, dyes, nonvolatile solvents or diluents (water soluble and insoluble), pearlescent aids, foam boosters, preservatives, heat transfer agents, proteins, sunscreens, niacinamide, or combinations thereof. In one example, the filaments of the present invention may comprise processing aids and/or materials that provide a signal (visual, audible, smell, feel, taste) that identifies when one or more of the active agents within the filament, web or shaving aid has been released from the filament. Suitable non-water soluble filament forming materials and filaments include for example polyamides and polyesters and mixtures thereof. In one embodiment the filament and or shaving aid are substantially free of said non water soluble polymers.

Filament-Forming Composition

The filaments of the present invention are made from a filament-forming composition. The filament-forming composition is a polar-solvent-based composition. In one example, the filament-forming composition is an aqueous composition comprising one or more filament-forming materials and optionally one or more additives and or active agents. The filament forming materials are preferably water soluble materials.

The filament-forming composition of the present invention may have a shear viscosity as measured according to the Shear Viscosity Test Method described herein of from about 1 Pascal·Seconds to about 25 Pascal·Seconds and/or from about 2 Pascal·Seconds to about 20 Pascal·Seconds and/or from about 3 Pascal·Seconds to about 10 Pascal·Seconds, as measured at a shear rate of 3,000 sec$^{-1}$ and at the processing temperature (50° C. to 100° C.).

The filament-forming composition may be processed at a temperature of from about 50° C. to about 100° C. and/or from about 65° C. to about 95° C. and/or from about 70° C. to about 90° C. when making filaments from the filament-forming composition.

In one example, the filament-forming composition may comprise at least 20% and/or at least 30% and/or at least 40% and/or at least 45% and/or at least 50% to about 90% and/or to about 85% and/or to about 80% and/or to about 75% by weight of one or more filament-forming materials, one or more additives, and mixtures thereof. The filament-forming composition may comprise from about 10% to about 80% by weight of a polar solvent, such as water.

The filament-forming composition may exhibit a Capillary Number of at least 1 and/or at least 3 and/or at least 5 such that the filament-forming composition can be effectively polymer processed into a hydroxyl polymer fiber.

The Capillary number is a dimensionless number used to characterize the likelihood of this droplet breakup. A larger capillary number indicates greater fluid stability upon exiting the die. The Capillary number is defined as follows:

$$Ca = \frac{V * \eta}{\sigma}$$

V is the fluid velocity at the die exit (units of Length per Time),
η is the fluid viscosity at the conditions of the die (units of Mass per Length*Time),
σ is the surface tension of the fluid (units of mass per Time$^2$). When velocity, viscosity, and surface tension are expressed in a set of consistent units, the resulting Capillary number will have no units of its own; the individual units will cancel out.

The Capillary number is defined for the conditions at the exit of the die. The fluid velocity is the average velocity of the fluid passing through the die opening. The average velocity is defined as follows:

$$V = \frac{Vol'}{Area}$$

Vol'=volumetric flowrate (units of Length' per Time),
Area=cross-sectional area of the die exit (units of Length$^2$).

When the die opening is a circular hole, then the fluid velocity can be defined as $$V = \frac{Vol'}{\pi * R^2}$$

R is the radius of the circular hole (units of length).
The fluid viscosity will depend on the temperature and may depend of the shear rate. The definition of a shear thinning fluid includes a dependence on the shear rate. The surface tension will depend on the makeup of the fluid and the temperature of the fluid.

In a filament spinning process, the filaments need to have initial stability as they leave the die. The Capillary number is used to characterize this initial stability criterion. At the conditions of the die, the Capillary number should be greater than 1 and/or greater than 4.

In one example, the filament-forming composition exhibits a Capillary Number of from at least 1 to about 50 and/or at least 3 to about 50 and/or at least 5 to about 30. The filament-forming composition of the present invention may have a shear viscosity of from about 1 Pascal·Seconds to about 25 Pascal·Seconds and/or from about 2 Pascal·Seconds to about 20 Pascal·Seconds and/or from about 3 Pascal·Seconds to about 10 Pascal·Seconds, as measured at a shear rate of 3,000 sec$^{-1}$ and at the processing temperature (50° C. to 100° C.).

The filament-forming composition may be processed at a temperature of from about 50° C. to about 100° C. and/or from about 65° C. to about 95° C. and/or from about 70° C. to about 90° C. when making fibers from the filament-forming composition.

In one example, the non-volatile components of the spinning composition may comprise from about 20% and/or 30% and/or 40% and/or 45% and/or 50% to about 75% and/or 80% and/or 85% and/or 90%. The non-volatile components may be composed of filament-forming materials, such as backbone polymers, actives and combinations thereof. The volatile component of the spinning composition will comprise the remaining percentage and range from 10% to 80%.

The filament-forming composition may exhibit a Capillary Number of at least 1 and/or at least 3 and/or at least 5 such that the filament-forming composition can be effectively polymer processed into a hydroxyl polymer fiber.

The Capillary number is a dimensionless number used to characterize the likelihood of this droplet breakup. A larger capillary number indicates greater fluid stability upon exiting the die. The Capillary number is defined as follows:

$$Ca = \frac{V * \eta}{\sigma}$$

V is the fluid velocity at the die exit (units of Length per Time),
η is the fluid viscosity at the conditions of the die (units of Mass per Length*Time),
σ is the surface tension of the fluid (units of mass per Time$^2$). When velocity, viscosity, and surface tension are expressed in a set of consistent units, the resulting Capillary number will have no units of its own; the individual units will cancel out.

The Capillary number is defined for the conditions at the exit of the die. The fluid velocity is the average velocity of the fluid passing through the die opening. The average velocity is defined as follows:

$$V = \frac{Vol'}{Area}$$

Vol'=volumetric flowrate (units of Length$^3$ per Time),
Area=cross-sectional area of the die exit (units of Length$^2$).

When the die opening is a circular hole, then the fluid velocity can be defined as $$V = \frac{Vol'}{\pi * R^2}$$

R is the radius of the circular hole (units of length).

The fluid viscosity will depend on the temperature and may depend of the shear rate. The definition of a shear thinning fluid includes a dependence on the shear rate. The surface tension will depend on the makeup of the fluid and the temperature of the fluid.

In a filament spinning process, the filaments need to have initial stability as they leave the die. The Capillary number is used to characterize this initial stability criterion. At the conditions of the die, the Capillary number should be greater than 1 and/or greater than 4.

In one example, the filament-forming composition exhibits a Capillary Number of from at least 1 to about 50 and/or at least 3 to about 50 and/or at least 5 to about 30.

In one example, the filament-forming composition may comprise one or more antiblocking and/or detackifying agents. Non-limiting examples of suitable antiblocking and/or detackifying agents include starches, modified starches, crosslinked polyvinylpyrrolidone, crosslinked cellulose, microcrystalline cellulose, silica, metallic oxides, calcium carbonate, talc and mica.

Additives and or active agents of the present invention may be added to the filament-forming composition prior to and/or during filament formation and/or may be added to the filament after filament formation. For example, a perfume active agent may be applied to the filament and/or web comprising the filament after the filament and/or web according to the present invention are formed. In another example, additives or active agents, which may not be suitable for passing through the spinning process for making the filament, may be applied to the filament and/or web comprising the filament after the filament and/or web according to the present invention by any suitable methods including coating as discussed herein are formed.

Web

One or more, and/or a plurality of water soluble filaments of the present invention may form a web such as a nonwoven web by any suitable process known in the art. The web may be used as a form to deliver the water-soluble filament forming materials preferably lubricating filament forming materials and optionally the skin care active agents from the filaments of the present invention when the web is exposed to conditions of intended use of the filaments and/or nonwoven web i.e. shaving. The webs may have a basis weight of from about 40 gsm to about 250 gsm.

Even though the filament and/or web of the present invention are in solid form, the filament-forming composition used to make the filaments of the present invention may be in the form of a liquid.

In one example, the web comprises a plurality of identical or substantially identical, from a compositional perspective, water soluble filaments. The web may also comprise two or more different filaments according to the present invention. Non-limiting examples of differences in the filaments may be physical differences such as differences in diameter, length, texture, shape, rigidness, elasticity, and the like; chemical differences such as crosslinking level, water solubility, melting point, Tg, active agent, filament-forming material, color, level of active agent, level of filament-forming lubricating material, presence of any coating on filament, and the like; differences in whether the filament loses its physical structure when the filament is exposed to conditions of intended use; differences in whether the filament's morphology changes when the filament is exposed to conditions of intended use; and differences in rate at which the filament dissolves when exposed to conditions of intended use. Two or more filaments within the web may comprise the same filament-forming material, but have different active agents. For example, this may be the case where the different active agents may be incompatible with one another. The web may optionally also comprise one or more non-water soluble filaments.

The web may be provided as a single layer or may comprise at least two layers, preferably a plurality of layers. Each layer of the web may be different or identical in terms of physical or chemical properties as discussed hereinabove. In one embodiment, the web may comprise from 2 to 12 layers produced using individual webs with a basis weight of from 40 to 190 gsm. The layers are typically superimposed upon one another to a form a stack.

In one example, the single layer web of the present invention exhibits a thickness of greater than 0.01 mm and/or greater than 0.05 mm and/or greater than 0.1 mm and/or to about 20 mm and/or to about 10 mm and/or to about 5 mm and/or to about 2 mm and/or to about 0.5 mm and/or to about 0.3 mm as measured by the Thickness Test Method described herein. The layers and or webs preferably each have a uniform thickness.

The filaments of the invention and the webs formed therefrom may be selected to obtain a desirable rate of dissolution of the filaments or webs in the conditions of intended use. In particular, the use of multiple layered webs enables the rate of dissolution to be controlled particularly during multiple shaving events thereby ensuring that sufficient lubricant and or skin actives are delivered during each shaving event whilst ensuring the structural integrity of the web and preventing premature depletion of the web. Multilayered webs can also provide a consumer desirable attribute delivering a soft and conformable shaving aid.

In one example, each individual layer of the web (in the absence of any coating) of the present invention exhibits an average dissolution time per g of sample of less than 120 and/or less than 100 and/or less than 80 and/or less than 55 and/or less than 50 and/or less than 40 and/or less than 30 and/or less than 20 seconds/gram (s/g) as measured according to the Dissolution Test Method described herein.

In another example, the web of the present invention comprising a plurality of layers (in the absence of any coating) exhibits an average dissolution time per g of sample of less than 5000, and or less than 4000 and/or less than 3500 seconds/gram s/g as measured according to the Dissolution Test Method described herein.

The web may comprise at least 30% by weight of filaments of water soluble filaments, or at least 40% or at least 50% or at least 50% or at least 60% or at least 70% or at least 80% or at least 90% by weight of water soluble filaments.

Impregnated/Coated Web

The web of the present invention may be further coated with one or more additives such as skin care active agents by any means known in the art, including but not limited to spray coating, dip coating, printing and/or slot coating in addition to or in the absence of any coating of individual filaments. Preferably spray coating is employed to create a well-controlled distribution of the additive such as the skin care active agent over the surface of the web. Preferably the active is uniformly applied and has the required characteristics to enable the additive to wick into the web and thereby not remain solely on the surface of the web. This may be facilitated by the addition of actives to reduce surface tension or by applying the skin care active agent at elevated temperatures so as to reduce its viscosity.

The coating may be uniformly applied over substantially the entire the upper skin facing surface and or lower surface of the web or may be applied in a continuous or discontinuous pattern. If multiple layers of webs are used then all or at least one of the surfaces of one of the web layers may be coated with an additive in continuous or discontinuous patterns. This may further facilitate the provision of a desirable rate of dissolution of the web over multiple usage events.

The coating may be a liquid or paste at ambient conditions or it may be a solid with a melting point of 40-90° C., even more preferably between 40-60° C. The coating may be homogeneous or it may contain a dispersed particulate phase.

The coating may comprise hydrophilic or hydrophobic skin care active agent. The coating preferably comprises a hydrophobic skin care active agent. This provides the benefit of treating the skin and controlling the rate of dissolution of the web particularly during multiple shaving events thereby ensuring that sufficient lubricant and or skin actives are delivered during each shaving event whilst ensuring the structural integrity of the web and preventing premature depletion of the web and skin active agents. Preferably the coating may comprise materials selected from petrolatum, PDMS, polyethylene oxide, a wax or mixtures thereof. In one example the coating is comprised of at least 90%, preferably 100% petrolatum. The amount of coating applied to the web is from 4:1 to 1:8 (web:coating) weight ratio.

In one example, the coated single layer web of the present invention exhibits an average dissolution time per g of sample of less than 120 and/or less than 100 and/or less than 80 and/or less than 55 and/or less than 50 and/or less than 40 and/or less than 30 and/or less than 20 seconds/gram (s/g) as measured according to the Dissolution Test Method described herein.

In another example, the coated multi-layer web of the present invention exhibits an average dissolution time per g of sample of less than 1500 and/or less than 1400 and/or less than 1300 and/or less than 1200 seconds/gram s/g as measured according to the Dissolution Test Method described herein.

Bonded/Laminated Web

In one embodiment the web may comprise from at least two to about 20 layers, preferably from 2 to 15 layers, even more preferably from 5 to 12 layers. The number of layers required may depend upon the basis weight of each individual web. In order to ensure the integrity of the multilayer web, such multilayer webs may be bonded to form a laminate using for example stacking and compression and or bonding techniques whereby the layers of web are superimposed and bonded together to form a laminate. The compression or bonding techniques include but are not limited to the application of heat, pressure, ultrasound and/or water or a combination thereof.

In one embodiment, the multiple layered web may be formed into a parent roll, which may be subsequently unwound and molded into the desired shape as discussed below or using a similar molding operation.

Multiple layered laminated webs may be formed by superimposing the layers of the web, preferably coated layers, within a mould or form that preferably has the desired shape and size for the razor article for which it is to be employed. The layers of the web maybe cut to size prior to insertion within the mold or this may be achieved during the lamination step itself. In a preferred embodiment, the resultant laminate web is bonded at least at the outer peripheral edges of the web or the desired in use shape and size. In this manner, the web retains both structural integrity and conformability when in planar view. The resulting laminate therefore has lower density in the center of the laminate than at the 'sealed' or bonded peripheral edges. The conditions for creating this laminate are selected dependant on the filament forming materials, web formation and the nature of the coating employed. In an alternative embodiment, the layers of web are bonded together over at least a portion of the surface of the web, preferably substantially the entire the surface of the web. The bonding may be in a continuous or discontinuous pattern. The lamination of the web provides structural integrity thereto and may be utilized to control the rate of dissolution thereof in use.

In one embodiment the shaving aid may also comprise a web formed of nano-filaments. The web can be a single layer or can be multiple layers. In one embodiment, the shaving aid comprises a conventionally extruded or molded water soluble shaving aid and/or a fibrous substrate comprising a filament is accompanied with the nano-filament web coating at least a portion of the shaving aid that touches the skin during a normal shaving stroke. In another embodiment, more than one nano-filament web is applied onto the shaving aid. Without intending to be bound by theory, it is believed that adding the one or more nano-filament webs can provide increased lubrication during the initial uses of the shaving aid as the nano-filaments can be selected to dissolve within the first shave thereby releasing an initial burst of lubricants. Where co-axial nano-filaments are used, such as those comprising a silicone or other skin care active in the core, the shaving aid can also provide skin care benefits during the initial shave due to the quick dissolving and breakdown of the co-axial nano-filaments. Mixtures of nano-fibers and co-axial nano-filaments can also be used, for example in one embodiment, the shaving aid comprises a nano-filament web and a second web made up of co-axial nano-filaments.

While it is possible to form a shaving aid comprising webs of filaments, the nano-filaments would likely be used as a web or plurality of laminated webs coating at least a portion of the shaving aid. In one embodiment, the shaving aid comprises from about 0.01% to 30% by weight, of said nano-filament, co-axial nano-filaments, or a combination thereof, or from about 0.1% to about 5%, or from about 1% to about 3%.

In one embodiment, at least one of the nano-filaments forming the web has a span of at least 30 μm between intersections with other nano-filaments in the shaving aid. The span can be from 10 μm to about 100 μm. In one embodiment, the nano-filament web has a thickness of from about 0.01 mm to about 5 mm. In one embodiment, the shaving aid comprises a plurality of such webs. In one embodiment, at least a portion of said skin contacting portion has a surface coating, said surface coating comprising said nano-filament, preferably wherein at least 20%, or at least 50%, up to 80% or up to 100% of the skin contacting portion, by surface area is covered by said surface coating. In one embodiment, the surface coating has a thickness of from about 0.01 mm to about 20 mm.

Hair Removal Head

According to the embodiments, the filaments find particular application for hair removal devices. In one example, the filaments are located on the housing of a hair removal device such as a razor cartridge or on a shaving aid therefore.

Hair removal devices generally comprise a hair removal head and a handle or grip portion, upon which the hair removal head is mounted. The hair removal device can be manual or power driven and can be used for wet and/or dry applications. The hair removal head can include a wide scraping surface such as where the hair removal device is used with a depilatory, or be a razor cartridge or foil where the device is a shaving razor. The hair removal head may be replaceable and/or pivotally connected to a cartridge connecting structure and in turn or independently (e.g. permanently fixed) to a handle. In some embodiments, the cartridge connecting structure includes at least one arm to releasably engage the hair removal head.

The hair removal head typically comprises one or more elongated edges usually positioned between a first and second end, said one or more elongated edges comprising a tip extending towards said first end. Where the hair removal head is a razor cartridge the one or more elongated edges can include blades. Such embodiments typically comprise a housing and blades contained therein.

The filament or web thereof may be located on at least a portion of the housing for example on the skin contacting surface thereof and or may be provided on the surface of, or integral with a shaving aid of either a conventional or filament formed nature. For example, U.S. Pat. No. 7,168,173 generally describes a FUSION® razor that is commercially available from The Gillette Company and which includes a razor cartridge with multiple blades. Additionally, the razor cartridge may include a guard as well as a skin engaging member. A variety of razor cartridges can be used in accordance with the present invention. Non-limiting examples of suitable razor cartridges, with and without fins, guards, and/or shave aids, include those marketed by The Gillette Company under the FUSION®, and VENUS® product lines as well as those disclosed in U.S. Pat. Nos. 7,197,825, 6,449,849, 6,442,839, 6,301,785, 6,298,558; 6,161,288, and U.S. 2008/060201. Those of skill in the art will understand that the shaving aid defined herein can be used with any currently marketed system or disposable razor, including those having 2, 3, 4 or 5 blades. In such a case, the hair removal device is a razor, the hair removal head is a razor cartridge and the one or more elongated edges are blades. Another example of a hair removal device is a scraping tool for use with a hair removal composition, i.e. a depilatory.

In some embodiments, the shaving aid is located on the portion of the cartridge that contacts skin during the hair removal process, forward and/or aft of the blades. A feature "forward" of the one or more elongated edges, for example, is positioned so that the surface to be treated with by the hair removal device encounters the feature before it encounters the elongated edges. A feature "aft" of the elongated edge is positioned so that the surface to be treated by the hair removal device encounters the feature after it encounters the elongated edges. Where more than one shaving aid is provided on the hair removal device, they can be the same (identical) or different, in terms of physical shape/structure and/or chemical composition.

In some particular embodiments, a plurality (e.g. 2, a first and second) of shaving aids may be provided on the hair removal head, with the first shaving aid comprising the same composition or different. These shaving aids may be placed collectively (for example adjacent to one another) ahead of or behind the elongated edges (e.g. blades on a razor cartridge), including side by side, or separately with one ahead of the elongated edges and the other behind.

In another embodiment at least a portion of the shaving aid may not be linear for example angled or curvilinear. Curvilinear as defined herein means that at least a portion is curved such that it does not form a straight line. Where at least two shaving aids are provided, they can also be positioned relative to one another such that they do not form a straight line.

In some embodiments, the curved or angled nature of the shaving aid is such that it forms at least a partial ring. A partial ring, as defined herein, means that the structure has at least two curved or angled sections which are concave to form an inner region. The partial ring can also include a curved or angled portion which is positioned convex to said inner region. One or more of said shaving aids may also be positioned relative to one another to form a full ring. The ring can be formed by a single shaving aid but two or more can be touching at or about their terminal ends, or even overlapping, to form such a ring.

The shaving aids may be free standing utilizing a suitable attachment means such as adhesive, use of mechanical retention features or may be contained at least partially within a container. For embodiments comprising more than one shaving aid, the filaments of the present invention may be present on one or more of the shaving aids present or all of the shaving aids or none of the shaving aids.

The hair removal head may comprise a conventional shaving aid comprising a lubricant such as water soluble polymer typically intended to provide lubrication in-use in a non-filament form. Examples of water soluble polymers include polyethylene oxide, polyvinyl pyrrolidone, polyacrylamide, polyhydroxymethacrylate, polyvinyl imidazoline, polyethylene glycol, polyvinyl alcohol, polyhydroxyethymethacrylate, silicone polymers, and a mixture thereof. In some embodiments, said water soluble polymer is selected from the group consisting of poly vinyl alcohol, polyethylene oxide, copolymers of polyethylene and polypropylene oxide, polyethylene glycol, and mixtures thereof.

The water-soluble polymer will preferably comprise at least about 50%, more preferably at least about 60%, by weight of the shaving aid, up to about 99%, (or up to about 90% of the lubricating material). For example, the water-soluble polymer may be present at an amount of at least about 50%, preferably from about 50% to about 99.9%, more preferably from about 60% to about 95% (e.g. from about 90% to about 95%) and even more preferably from about 70% to about 90% by weight of the lubricating material. The more preferred water soluble polymers are the polyethylene oxides generally known as POLYOX (available from Union Carbide Corporation) or ALKOX® (available from Meisei Chemical Works, Kyoto, Japan). The water-soluble polymer, (especially these polyethylene oxides), will preferably have average molecular weights of at least about 20,000, at least about 50,000, at least about 100,000 or from about 100,000 to 6 million, preferably about 300,000 to 5 million. A particularly preferred polyethylene oxide comprises a blend of about 40% to 80% of polyethylene oxide having an average mol·wt. of about 5 million (e.g. POLYOX COAGULANT) and about 60% to 20% of polyethylene oxide having an average mol·wt. of about 300,000 (e.g. POLYOX WSR-N-750). The polyethylene oxide blend may also advantageously contain up to about 10% (for example about 5%) by weight of a low mol·wt. (i.e. MW<10,000) polyethylene glycol such as PEG-100.

The conventional shaving aid may further comprise a water-insoluble polymer, e.g. in which the water-soluble polymer is dispersed, which may be referred to as a water-insoluble matrix. Preferably, the water insoluble polymer is present at a level of from about 0% to about 50%, more preferably about 5% to about 40%, and even more preferably about 15% to about 35% by weight of the shaving aid member. Suitable water-insoluble polymers which can be used include polyethylene (PE), polypropylene, polystyrene (PS), butadiene-styrene copolymer (e.g. medium and high impact polystyrene), polyacetal, acrylonitrile-butadiene-styrene copolymer, ethylene vinyl acetate copolymer, polyurethane, and blends thereof such as polypropylene/polystyrene blend or polystyrene/impact polystyrene blend. One preferred water-insoluble polymer is polystyrene, preferably a general purpose polystyrene, such as NOVA C2345A, or a high impact polystyrene (HIPS) (i.e. polystyrene-butadiene), such as BASF 495F KG21. The strip or any portion should contain a sufficient quantity of water-insoluble polymer to provide adequate mechanical strength, both during production and use. In some embodiments, the shaving aid comprises any other ingredients commonly found in commercially available shaving aid members, such as those used on razor cartridges by GILLETTE®, SCHICK® or BIC®. Non-limiting examples of such shaving aid members include those disclosed in U.S. Pat. Nos. 6,301,785, 6,442,839, 6,298,558, 6,302,785, and U.S Patent Pubs 2008/060201, and 2009/0223057.

The conventional shaving aids may be fabricated by any appropriate method, including injection molding, pressing, impregnation, spray-coating, calendaring and extrusion, the latter being preferred. All of the components of the aid can be blended prior to molding or extrusion. For best results, it is preferred that the components are dry. In summary, the method comprises the steps of providing a feed comprising a water-soluble polymer; a water insoluble polymer; preferably heating said feed to a temperature of from 120° C. to 200° C., and molding, pressing, impregnating, spray-coating, calendaring and/or extruding said feed to form a shaving aid member. The filament(s) or web(s) of the invention may be located on the skin contacting surface of such a conventional shaving aid and attached thereto using any means known in the art.

Method for Making the Filament, Web and or Shaving Aid

The filaments of the present invention may be made by any suitable process. A non-limiting example of a suitable process for making the filaments is described below.

In one example, a method for making a filament according to the present invention comprises the steps of:

a. providing a filament-forming composition preferably comprising one or more water soluble filament-forming materials and optionally one or more additives and or skin care active agents; and b. spinning the filament-forming composition into one or more filaments During the spinning step, any volatile solvent, preferably water, present in the filament-forming composition is removed, such as by drying, as the filament is formed. In one example, greater than 50% and/or greater than 70% and/or greater than 90% of the weight of the filament-forming composition's volatile solvent, such as water, is removed during the spinning step, such as by drying the filament being produced.

The filament-forming composition is spun into one or more filaments by any suitable spinning process, such as electro-spinning, meltblowing and/or spinbonding. In one example, the filament-forming composition is spun into a plurality of filaments by meltblowing. For example, the filament-forming composition may be pumped from an extruder to a meltblown spinnerette. Upon exiting one or more of the filament-forming holes in the spinnerette, the filament-forming composition is attenuated with air to create one or more filaments. The filaments may then be dried to remove any remaining solvent used for spinning, such as the water. In another example, the filament forming composition is spun into a plurality of filaments utilizing electrospinning techniques known in the art. The filament forming composition is pumped from the making vessel to an electrospinning tip wherein a charge is applied. The filament is attenuated in air during attraction towards the receiving drum or belt. The filaments can be removed from the belt and applied to the hair removal head by any means known in the art. Alternatively a base substrate or shaving aid component or components can be attached to the receiving drum and the filaments form a coating on the upper surface of the shaving aid.

Methods of Making Nano-Filament Webs

In one embodiment, where the shaving aid comprises a nano-filament web, the nano-filament can be formed by electrospinning techniques such as those disclosed in US2014/0277572, U.S. Pat. No. 7,390,760, and WO2001051690.

As used herein, the term "electrospinning" refers to a technology which can be used to produce nano-sized fibers referred to as electrospun fibers from a solution using interactions between fluid dynamics and charged surfaces. Additionally, those of skill in the art will understand that electrospinning can also be used to create larger diameter fibers such as those where the diameter is greater than 1 nm (which can be used to create filaments). In general, formation of the electrospun fiber involves providing a solution to an orifice in a body in electric communication with a voltage source, wherein electric forces assist in forming fine fibers that are deposited on a surface that may be grounded or otherwise at a lower voltage than the body. In electrospinning, a polymer solution or melt provided from one or more needles, slots or other orifices is charged to a high voltage relative to a collection grid. Electrical forces overcome surface tension and cause a fine jet of the polymer solution or melt to move towards the grounded or oppositely charged collection grid. The jet can splay into even finer fiber streams before reaching the target and is collected as an interconnected web of small fibers. Specifically, as the solvent is evaporating (in processes using a solvent), this liquid jet is stretched to many times it original length to produce continuous, ultrathin fibers of the polymer. The dried or solidified fibers can have diameters of about 40 nm, or from about 10 to about 100 nm, although 100 to 500 nm fibers are commonly observed. Various forms of electrospun nanofibers include branched nanofibers, tubes, ribbons and split nanofibers, nanofiber yarns, surface-coated nanofibers (e.g., with carbon, metals, etc.), nanofibers produced in a vacuum, and so forth. The production of electrospun fibers is illustrated in many publication and patents, including, for example, P. W. Gibson et al, "Electrospun Fiber Mats: Transport Properties," AIChE Journal, 45(1): 190-195 (January 1999), which is hereby incorporated herein by reference.

In one embodiment of the present invention, the method of making a shaving aid comprising: extruding a shaving aid through a die to form an extruded shaving aid, said shaving aid having a skin contacting surface; and electrospinning a nano-filament onto a portion of the skin contacting surface to form a coated shaving aid. In one embodiment, said extruded shaving aid is allowed to cool (such as to 25 C.° and/or harden before the step of electrospinning. In another embodiment, the method further comprises a step of cutting a portion of said coated shaving aid to form a prepared shaving aid. In one embodiment, multiple layers of the web are used, the web can be formed, then folded before being applied over a portion of the shaving aid.

Coating Filaments with Additives

The filaments of the present invention may be coated with additives or active agents by any means known in the art, but not limited to spray coating, printing, dip coating or combinations thereof.

Formation of the Web

The filaments of the present invention may be collected on a belt, such as a patterned belt to form a web comprising the filaments. Non-water soluble filaments may be also be fed onto the belt to form a web comprising both water soluble and non-water soluble filaments.

In one embodiment, the web may be coated with an additive and or skin care active by any means known in the art, including but not limited to spray coating, dip coating, printing and/or slot coating. Preferably spray coating is employed. In one non-limiting example, the coating is applied using an X-Y table to create a well-controlled distribution of the additive such as the skin care active agent over at least one surface of the web.

In another embodiment, at least two layers of the web (coated or uncoated) are bonded to form a laminate by any means known in the art. Typically this may be achieved by utilization of a mould to form the desired shape and size such as a shaving aid and the addition of heat, pressure and water or combinations thereof. In one example, the coated web layers are bonded using a combination of heat, pressure and water applied to the web. The water used may be present as steam or more preferably may be applied to the web as a fine spray. In another example, the coating used is thermosetting and heat and pressure only are used.

Methods of Use

The filament and webs optionally comprising one or more skin care active agents according to the present invention may be utilized in a method for treating skin during the shaving process. The method of treating the skin may comprise one or more steps including (a) attaching the filament or web or shaving aid thereof to the razor or to the housing or to the shaving aid; (b) contacting the razor with water; (c) contacting the razor with the skin and moving across the skin in a manner consistent with removing the hair; (d) rinsing and drying and the skin; and (e) combinations thereof.

Non-limiting Examples

Example 1-10: Water Soluble Filaments

Examples 1-10 are produced by using a small-scale apparatus comprising a pressurized tank suitable for batch operations is filled with a filament-forming composition, for example a filament-forming composition that is suitable for making filaments useful as articles for razors. The steps for making the filament forming composition comprise;

i) Disperse the lubricating materials in water (temp) and mix with mechanical agitation (speed). The materials can be mixed together or can be made into separate pre-mixes and then combined.
ii) Add any additional ingredients such as additives or skin care active agents.
iii) If necessary heat to 90° C. and continue to mix to form a uniform dispersion of the lubricating materials and any additional materials.
iv) Use above filament forming composition to spin into filaments A pump (for example a Zenith, type PEP II pump having a capacity of 5.0 cubic centimeters per revolution (cc/rev), manufactured by Parker Hannifin Corporation, Zenith Pumps division, of Sanford, N.C., USA) is used to pump the filament-forming composition to a die. The filament-forming composition's material flow to a die is controlled by adjusting the number of revolutions per minute (rpm) of the pump. Pipes are connected the tank, the pump, and the die in order to transport the filament-forming composition from the tank to the pump and into the die. The die has two or more rows of circular extrusion nozzles spaced from one another at a pitch of about 1.524 millimeters (about 0.060 inches). The nozzles have individual inner diameters of about 0.305 millimeters (about 0.012 inches) and individual outside diameters of about 0.813 millimeters (about 0.032 inches). Each individual nozzle is encircled by an annular and divergently flared orifice to supply attenuation air to each individual nozzle. The filament-forming composition that is extruded through the nozzles is surrounded and attenuated by generally cylindrical, humidified air streams supplied through the orifices encircling the nozzles to produce the filaments. Attenuation air is provided by heating compressed air from a source by an electrical-resistance heater, for example, a heater manufactured by Chromalox, Division of Emerson Electric, of Pittsburgh, Pa., USA. An appropriate quantity of steam is added to the attenuation air to saturate or nearly saturate the heated air at the conditions in the electrically heated, thermostatically controlled delivery pipe. Condensate is removed in an electrically heated, thermostatically controlled, separator. The filaments are dried by a drying air stream having a temperature of from about 149° C. (about 300° F.) to about 315° C. (about 600° F.) by an electrical resistance heater (not shown) supplied through drying nozzles (not shown) and discharged at an angle of about 90° relative to the general orientation of the filaments being spun. The filaments may be collected on a collection device, such as a belt or fabric, in one example a belt or fabric capable of imparting a pattern, for example a non-random repeating pattern to a nonwoven web formed as a result of collecting the filaments on the belt or fabric. The basis weight of the web was from 40 to 250 gsm.

Examples 11-14: Electrospun Water Soluble Filaments

Examples 11-14 are produced using a small scale electrospinning apparatus supplied by Spraybase, of Dublin, Ireland. Aqueous polymer solutions are prepared as described in examples 12-14. These solutions are then drawn into syringes which are coupled by luer locks to flexible PTFE tubing. The syringes are placed in a syringe pump supplied by Spraybase and the emitting end of the tubing is coupled to a metallic 20 gauge emitter by a luer lock. The metal emitter is then placed on a translating stage directly across from a rotating metal drum collector. The metal drum collector is covered with aluminum foil to allow easy sample recovery and storage. The entire system is controlled by a PC linked by USB. A metal pin provides charge to the emitter while the drum is grounded. A voltage difference between the emitter and the drum creates and electric field through which the polymer solutions are pumped at flow rates ranging from 0.4 mL/hr-0.8 mL/hr. The applied voltage ranges from 5 kV to 15 kV. The distance between the emitter tip and the collecting drum ranges from 15 cm to 30 cm. These process settings are tuned for each formulation until a stable Taylor cone is observed at the emitter tip as is familiar to anyone with skill in the art.

Specifically, for the coaxial fiber outlined in Example 11, an additional syringe pump is used for a total of 2 syringe pumps. A special coaxial emitter tip is used consisting of a 26 gauge needle concentrically mounted inside a 20 gauge needle supplied by Spraybase. The outer (sheath) fluid is pumped into the 20 gauge needle space while the inner (core) hydrophobic liquid is pumped into the 26 gauge needle space. The concentricity of the fluids is maintained as they enter the above mentioned electric field and are drawn by electrohydrodynamic forces into small diameter fibers. In this way, a dry PEO sheath encapsulates a hydrophobic liquid core. The flow rate for the inner liquid is ideally 0.04 mL/hr and the flow rate for the outer liquid can be 0.4 mL/hr.

Examples 1-5 Filaments

The following filament forming compositions were prepared:—

| Filament forming composition | | 1 % w/w | 2 % w/w | 3 % w/w | 4 % w/w | 5 % w/w |
|---|---|---|---|---|---|---|
| Lubricating Filament Forming Material | PVOH KL318 * | 12.50 | 0.00 | 12.50 | 12.50 | 12.50 |
| | PVA 420H * | 0.00 | 15.00 | 0.00 | 0.00 | 0.00 |
| | Polyox N750 ** | 0.00 | 0.00 | 0.00 | 2.38 | 2.38 |
| | Polyox N60K ** | 0.40 | 0.00 | 1.54 | 0.00 | 0.00 |
| | Polyox Coag ** | 0.00 | 0.55 | 0.00 | 0.23 | 0.23 |
| | Propylene Glycol ^ | 0.00 | 2.76 | 0.00 | 0.00 | 0.00 |
| | PEG 400 ^ | 0.00 | 0.00 | 3.51 | 1.88 | 6.25 |
| | PEG 300 ^ | 0.00 | 0.00 | 0.00 | 4.38 | 0.00 |
| Skin Care Active Agent | Tween 80 | 0.00 | 0.00 | 0.00 | 0.00 | 2.50 |
| Solvent | Water | 87.10 | 81.69 | 82.45 | 78.63 | 76.14 |

\* PVOH KL 318 and PVA420H supplied by Kuraray.
\*\* Polyox N750, N60K and Coag supplied by Dow Chemical,
^ PEG400 and 300 supplied by BASF.

The following filament compositions were formed therefrom

| Filament composition | | 1 % w/w dry filament | 2 % w/w dry filament | 3 % w/w dry filament | 4 % w/w dry filament | 5 % w/w dry filament |
|---|---|---|---|---|---|---|
| Lubricating Filament Forming Material | PVOH KL318 | 96.88 | — | 71.2 | 58.55 | 52.41 |
| | PVA 420H | — | 81.92 | — | — | — |
| | Polyox N750 | — | — | — | 11.12 | 9.96 |
| | Polyox N60K | 3.12 | — | 8.76 | — | — |
| | Polyox Coag | — | 2.99 | — | 1.05 | 0.94 |
| | Propylene Glycol | — | 15.08 | — | — | — |
| | PEG 400 | — | — | 19.99 | 8.78 | 26.20 |
| | PEG 300 | — | — | — | 20.49 | — |
| Skin Care Active Agent | Tween 80 | — | — | — | — | 10.48 |

Example Filaments 6-10

The following filament forming compositions were prepared:—

| Filament forming material | | 6 % w/w | 7 % w/w | 8 % w/w | 9 % w/w | 10 % w/w |
|---|---|---|---|---|---|---|
| Lubricating Filament Forming Material | PVOH KL318 * | 12.5 | 15.00 | — | — | 15.00 |
| | Polyox N750 ** | 2.5 | 2.5 | — | — | 2.5 |
| | Polyox Coag ** | 0.225 | 0.11 | — | — | 0.11 |
| | PEG 400 ^ | 5.00 | 5.00 | — | — | 5.00 |
| | Merquat 280 | — | — | 42 | — | — |
| | Merquat 2001 | — | — | — | 22 | — |
| Solvent | Water | 79.775 | 77.39 | 58 | 78 | 77.39 |

The following filaments were formed therefrom:—

| Filament composition | | 6<br>% w/w dry filament | 7<br>% w/w dry filament | 8<br>% w/w dry filament | 9<br>% w/w dry filament | 10<br>% w/w dry filament |
|---|---|---|---|---|---|---|
| Lubricating Filament Forming Material | PVOH KL318 | 61.80 | 66.30 | — | — | 83.3 |
| | Polyox N750 | 12.36 | 11.10 | — | — | 2.5 |
| | Polyox Coag | 1.11 | 0.49 | — | — | 0.1 |
| | PEG 400 | 24.72 | 22.11 | — | — | 5.00 |
| | Merquat 280 | — | — | 100.0 | — | — |
| | Merquat 2001 | — | — | — | 100 | — |

Examples 11-14

| Filament forming material | | 11<br>% w/w | 12<br>% w/w | 13<br>% w/w | 14<br>% w/w |
|---|---|---|---|---|---|
| Lubricating Filament Forming Material | Polyox N750 ** | 4 | 2 | 8 | 5 |
| | Polyox Coag ** | — | — | — | — |
| | PEG 400 ^ | — | — | — | — |
| | Polyox N60K | 1 | 1 | — | 1 |
| | Polyox N12K | — | 2 | — | — |
| | Pluronic F-127 | 1 | 1 | 2 | 1 |
| Solvent | Water | 94 | 94 | 90 | 93 |

The filaments exemplified below were produced from the filament forming compositions above;

| Filament composition | | 11<br>% w/w dry web | 12<br>% w/w dry web | 13<br>% w/w dry web | 14<br>% w/w dry web |
|---|---|---|---|---|---|
| Lubricating Filament Forming Material | Polyox N750 | 25.6 | 33.33 | 80 | 71.43 |
| | Polyox Coag | — | — | — | — |
| | PEG 400 | — | — | — | — |
| | Polyox N60K | 6.42 | 16.67 | — | 14.285 |
| | Polyox N12K | — | 33.33 | — | — |
| | Pluronic F-127 | 6.42 | 16.67 | 20 | 14.285 |
| Additive | DC200 200 cst | 61.56 | — | — | — |

Coatings

As discussed herein above the individual layers of the web may be coated. This may be performed using a spray coating device. This can either be manual with a controlled flow but uncontrolled delivery conditions. Preferably a device such as an X-Y table is employed which controls both the flow and the location of droplet delivery. Alternatively a spray gun may be employed using a flow rate in the range of 100-200 ml/min. The coating may be heated to improve flowability through the spray device.

The filaments or non-woven webs described in Examples 1-10 and 11-14 above may be coated. Examples of suitable coatings comprising skin care active agents are shown below.

| | | Coating | | |
|---|---|---|---|---|
| | | A<br>% w/w | B<br>% w/w | C<br>% w/w |
| Skin Care Active Agent | Petrolatum | 100.0 | 15.23 | — |
| | Silicone DC200 350 cst $ | — | 21.19 | — |
| | Softcat SL5 * | — | 10.60 | — |
| | Planell oil EU ^ | — | — | 16.25 |
| | Silwet L7210 + | — | 21.19 | 35.0 |
| | Cetyl alcohol | — | 26.50 | 27.0 |
| | Multiwax 180MH # | — | 5.29 | 5.5 |

Suppliers:
* - Dow Chemicals,
^ - Lonza,
$ - Dow Corning,
- Sonnenborn,
+ - Momentive Coatings B and C were manufactured in sanitized equipment. The making vessel is heated to 85° C. via a water bath or heating jacket and the lipophilic structurants are added (cetyl alcohol, Multiwax). The oil phase ingredients are then added and mixed until fully liquid. The heat is then reduced to 55° C. and the powder ingredients are added (SoftCat) and mixed until evenly dispersed. The mixture can then be cooled to room temperature and stored for coating or can be coated directly whilst molten. If a thick coating layer is required then the coating can also be poured into an appropriate mould and cooled to form a separate solid part.

Figure 4:
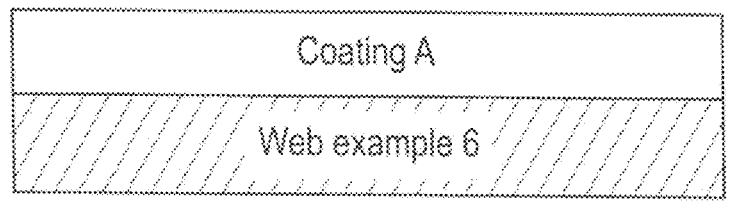
Figure 4:
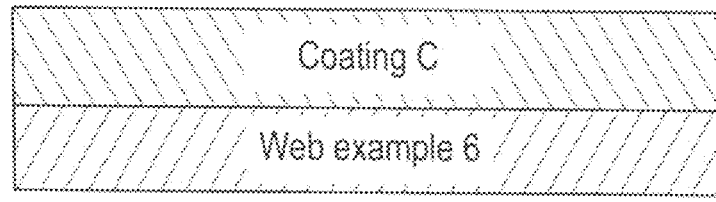
Figure 4:
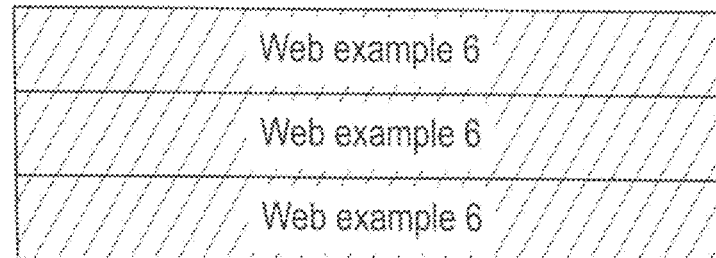
Figure 4:
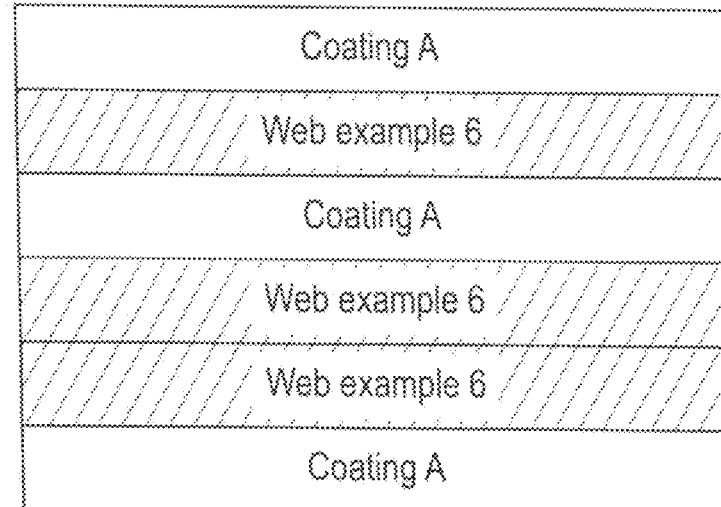

Single layers of coated webs or filaments can be employed for use on the razor cartridge. One example of this is to coat a single layer of the web produced in Example 6 above with 92 gsm of Coating A. This combination has been tested in the dissolution test below and is described as Example 6A (and depicted in FIG. 4).

Laminates

Multiple layers of the webs may be stacked together and compressed to form a laminate. The conditions required are dependent upon whether the layers of the webs are coated or uncoated. Typically the process requires the positioning of the stacked webs within a mould suitable for forming the shaving aid and the application of heat, pressure and optionally water or a thermo-setting material. According to the web and coating, formulation compression times in the range 2-7 min at conditions of 50-120° C. and 1000-2500 kgf are employed. A cooling time after compression is preferred.

The following laminated webs were prepared as indicated below and are depicted in FIGS. 1 to 4 (L1, L2, L3, 6, 6A, L6, L4 and L5).

1. Select filaments for laminate construction according to gsm of web required and type of coating to be employed. Coat the web or filaments with the coating selected,
2. Define number of web layers to be used and cut to appropriate size and record mass. The mass of the total web stack should be recorded.

3. If multiple coatings are being employed then the second coating is applied when the web stack is being assembled. It can be applied as a solid pre-formed sheet or by any known means such as slot coating on the web required.

4. For coating type A with no thermo set material present in the coating, a light application of water may be required to form the laminate. A fine spray is employed to evenly and lightly coat each web layer prior to stacking.

5. A suitable mould with cavities forming the parts suitable for later attachment to the razor is provided. This mould can apply pressure evenly over the whole surface of the laminate or more typically localize the pressure around the edge of the part to ensuring sealing.

6. The assembled web stack is then placed in the mould, and which is placed in a suitable hydraulic press with heated platens to reach the temperatures and pressures required. Typically the mould is around 12×12 cm2 in size to enable fitting into the press.

7. For coatings type B and C these will thermo set and form the laminate on heating and compression. A temperature of 50° C. for 2 mins at a load of 2000-2500 kgf is utilized.

8. For coating type A, typical conditions are 120° C. applied for 7 mins at 800-1000 kgf. The amount of water used to adjoin the layers will influence these conditions.

9. Extract the mould from the press and allow to cool for at least 5 mins with a weight on the mould to maintain a low pressure (typically 5 kg).

10. Once cooled, the formed laminate is removed from the mould and cut to shape if required. The laminate may then be attached to the razor cartridge housing by adhesive or any other suitable means.

| Web | Laminate | | | | | |
|---|---|---|---|---|---|---|
| | L1 Example 6 | L2 Example 6 | L3 Example 6 | L4 Example 6 | L5 Example 6 | L6 Example 6 |
| Web basis weight (gsm) | 190 | 190 | 40 | 190 | 190 | 190 |
| Number of layers of web | 5 | 2 | 12 | 3 | 3 | 1 |
| Coating 1 | A | A | C | — | A | C |
| Coating basis weight (gsm) | 50 | 65 | 40 | — | 92 | 1520 |
| Coating employed on all web layers | Yes | 2 layers | Yes | — | Yes | Yes |
| Coating 2 | — | B | — | — | — | — |
| Coating basis weight (gsm) | — | 462 | — | — | — | — |
| Coating employed on all web layers | — | — | — | — | — | — |

Using the Dissolution test method described herein, the rate of dissolution of the examples 6, 6A, L6, L4 and L5 is clearly shown below:—

| N = 3 | Example 6 1 Layer Uncoated (s/g) | Example 6A 1 Layer Coated (s/g) | Example L4 3 Layers Uncoated (s/g) | Example L5 3 Layers Coated (s/g) |
|---|---|---|---|---|
| Mean | 20.052 | 9.902 | 3293.450 | 1185.688 |
| St. Er. | 6.166 | 2.457 | 1512.277 | 162.951 |

As can be seen from the data above, formation of a laminated structure significantly increases dissolution time. This has the advantage of increasing the rate of dissolution and thereby controlling the rate at which the lubricating materials and or skin actives are delivered to the skin during the shaving process.

Figure 5:
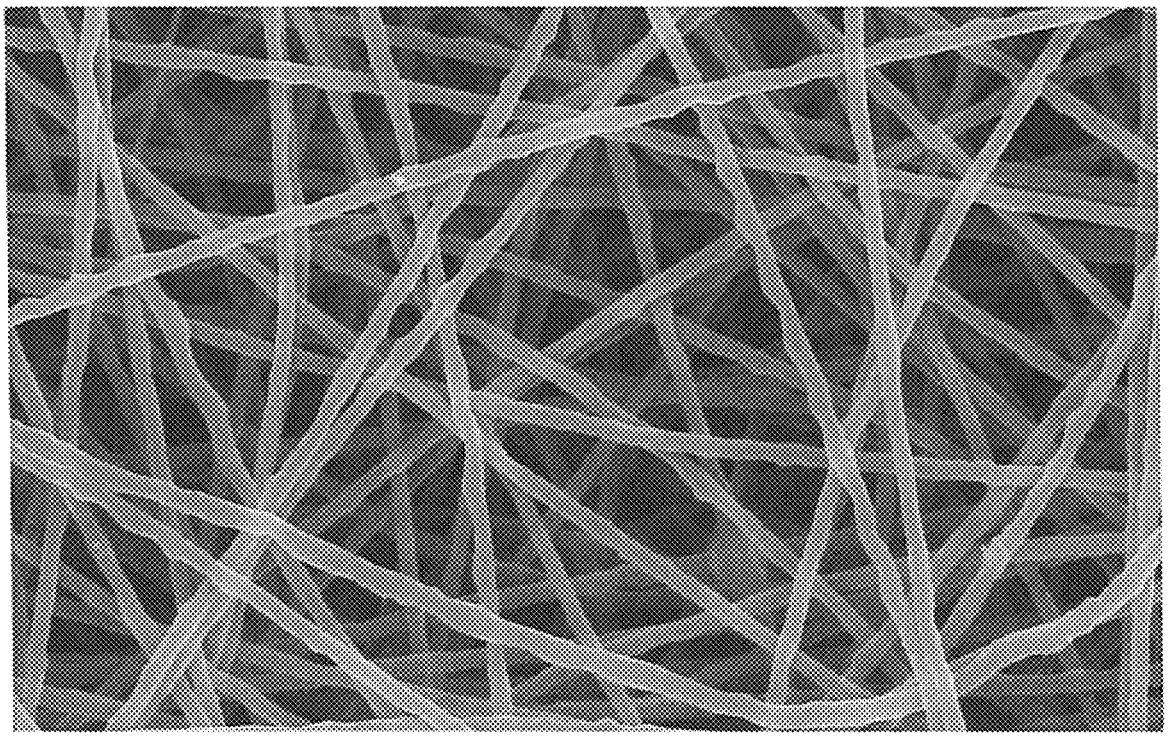
FIG. 5 is a microscopic image of a nano-filament in accordance with at least one embodiment of the present invention.

FIG. 5 shows a FESEM image of a nano-filament web in accordance with at least one embodiment of the present invention. This sample comprises 5% by weight of PEO having MW=900 kDa. Nano-fibers are measured having average diameter of about 337 nm.

Image analysis performed using Fiji (ImageJ)
Pixel ratio set by SEM scale bar
n=25 measurements taken per image, labeled, and reported Test Methods Unless otherwise indicated, all tests described herein including those described under the Definitions section and the following test methods are conducted on samples that have been conditioned in a conditioned room at a temperature of 73° F.±4° F. (about 23° C.±2.2° C.) and a relative humidity of 50%±10% for 2 hours prior to the test unless otherwise indicated. Samples conditioned as described herein are considered dry samples (such as "dry filaments") for purposes of this invention. Further, all tests are conducted in such conditioned room.

Water Content Test Method

The water (moisture) content present in a filament and/or web is measured using the following Water Content Test Method.

A filament and/or web or portion thereof ("sample") is placed in a conditioned room at a temperature of 73° F.±4° F. (about 23° C.±2.2° C.) and a relative humidity of 50%±10% for at least 24 hours prior to testing. The weight of the sample is recorded when no further weight change is detected for at least a 5 minute period. Record this weight as the "equilibrium weight" of the sample. Next, place the sample in a drying oven for 24 hours at 70° C. with a relative humidity of about 4% to dry the sample. After the 24 hours of drying, immediately weigh the sample. Record this weight as the "dry weight" of the sample. The water (moisture) content of the sample is calculated as follows:

$$\% \text{ Water (moisture) in sample} = 100\% \times \frac{(\text{Equilibrium weight of sample} - \text{Dry weight of sample})}{\text{Dry weight of sample}}$$

The % Water (moisture) in sample for 3 replicates is averaged to give the reported % Water (moisture) in sample.

Dissolution Test Method

Apparatus and Materials:
600 mL Beaker
Magnetic Stirrer (Labline Model No. 1250 or equivalent)
Magnetic Stirring Rod (5 cm)
Thermometer (1 to 100° C.+/−1° C.)
Template, Stainless Steel (3.8 cm×3.2 cm)
Timer (0-300 seconds, accurate to the nearest second)
35 mm Slide Mount having an open area of 3.8 cm×3.2 cm (commercially available from Polaroid Corporation)
35 mm Slide Mount Holder
Tap Water or equivalent having the following properties: Total Hardness=155 mg/L as CaCO3; Calcium content=33.2 mg/L; Magnesium content=17.5 mg/L; Phosphate content=0.0462

Figure 2:
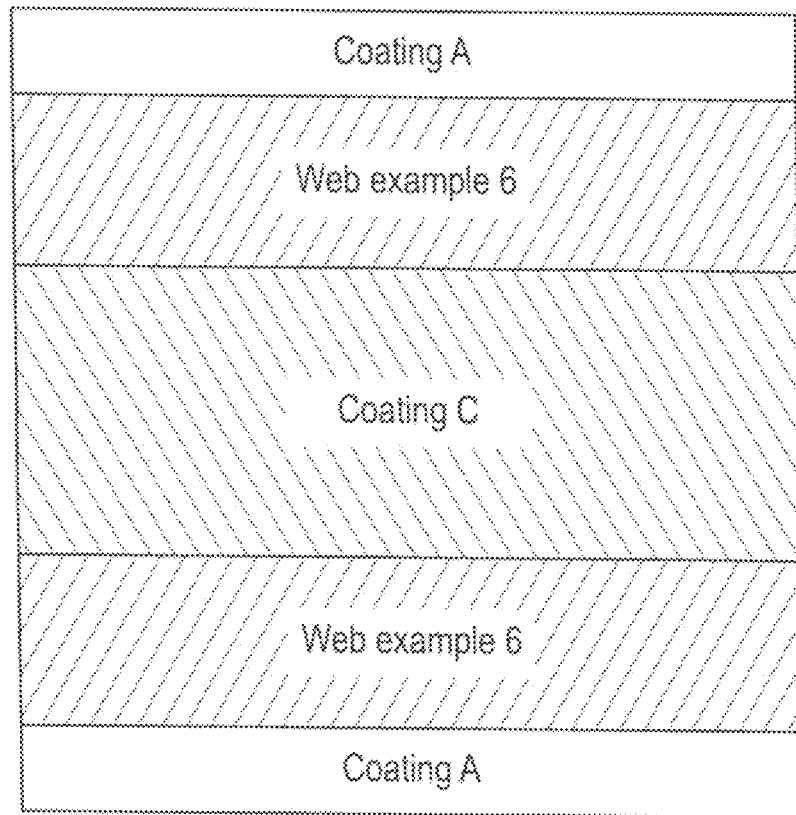
Figure 3:
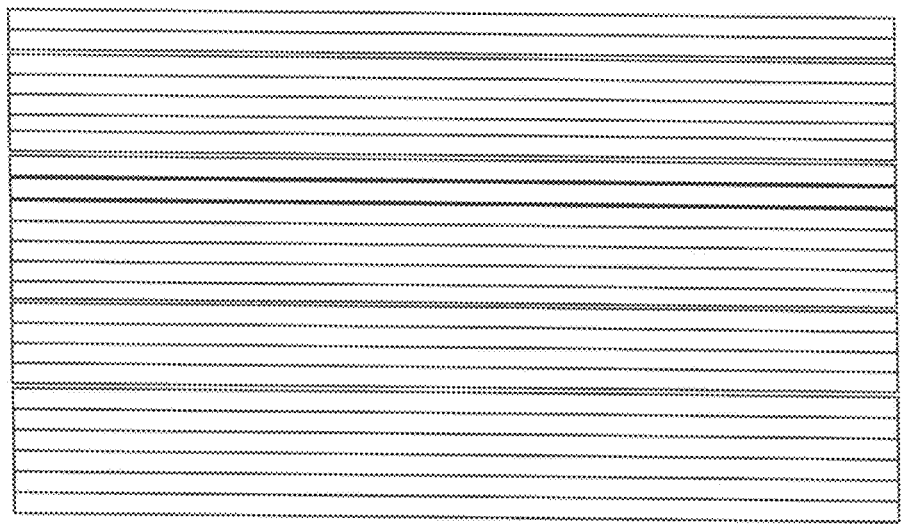

Sample Preparation:
1. Cut 3 test samples from the web to be tested ("sample") using the template to ensure that the sample fits within the 35 mm slide mount with open area dimensions 24×36 mm (i.e. 3.8 cm×3.2 cm specimen). Cut the samples from areas of the web equally spaced along the transverse direction of the web.
2. Lock each of the 3 samples in a separate 35 mm slide mount.
3. Place magnetic stirring rod into the 600 mL Beaker.
4. Obtain 500 mL or greater of Cincinnati city water and measure water temperature with thermometer and, if necessary, adjust the temperature of the water to maintain it at the testing temperature; namely, 5° C. Once the water temperature is at 5° C., fill the 600 mL beaker with 500 mL of the water.
5. Next, place the beaker on the magnetic stirrer. Turn the stirrer on, and adjust stir speed until a vortex develops in the water and the bottom of the vortex is at the 400 mL mark on the 600 mL beaker.
6. Secure the 35 mm slide mount with sample locked therein in a holder designed to lower the 35 mm slide mount into the water in the beaker, for example an alligator clamp of a 35 mm slide mount holder designed to position the 35 mm slide mount into the water present in the 600 mL beaker. The 35 mm slide mount is held by the alligator clamp in the middle of one long end of the 35 mm slide mount such that the long ends of the 35 mm slide mount are parallel to the surface of the water present in the 600 mL beaker. This set up will position the film or nonwoven surface perpendicular to the flow of the water. A slightly modified example of an arrangement of a 35 mm slide mount and slide mount holder are shown in FIGS. 1-3 of U.S. Pat. No. 6,787,512.
7. In one motion, the 35 mm slide mount holder, which positions the 35 mm slide mount above the center of the water in the beaker, is dropped resulting in the 35 mm slide mount becoming submerged in the water sufficiently such that the water contacts the entire exposed surface area of the film or nonwoven sample locked in the 35 mm slide mount. As soon as the water contacts the entire exposed surface area of the film or nonwoven start the timer. Disintegration occurs when the film or nonwoven breaks apart. When all of the visible web is released from the slide mount, raise the 35 mm slide mount out of the water while continuing to monitor the water for undissolved web fragments. Dissolution occurs when all web fragments are no longer visible in the water.
8. Three replicates of each sample are run.
9. Each disintegration and dissolution time is normalized by weight of the sample to obtain values of the disintegration and dissolution times per g of sample tested, which is in units of seconds/gram of sample (s/g). The average disintegration and dissolution times per g of sample tested of the three replicates are recorded.

Diameter Test Method

The diameter of a discrete filament or a filament within a web is determined by using a Scanning Electron Microscope (SEM) or an Optical Microscope and image analysis software. A magnification of 200 to 10,000 times is chosen such that the filaments are suitably enlarged for measurement. When using the SEM, the samples are sputtered with gold or a palladium compound to avoid electric charging and vibrations of the filament in the electron beam. A manual procedure for determining the filament diameters is used from the image (on monitor screen) taken with the SEM or the optical microscope. Using a mouse and a cursor tool, the edge of a randomly selected filament is sought and then measured across its width (i.e., perpendicular to filament direction at that point) to the other edge of the filament. A scaled and calibrated image analysis tool provides the scaling to get actual reading in μm. For filaments within a web, several filaments are randomly selected across the sample of the web using the SEM or the optical microscope. At least two portions the web (or web inside a product) are cut and tested in this manner Altogether at least 100 such measurements are made and then all data are recorded for statistical analysis. The recorded data are used to calculate average (mean) of the filament diameters, standard deviation of the filament diameters, and median of the filament diameters.

Another useful statistic is the calculation of the amount of the population of filaments that is below a certain upper limit. To determine this statistic, the software is programmed to count how many results of the filament diameters are below an upper limit and that count (divided by total number of data and multiplied by 100%) is reported in percent as percent below the upper limit, such as percent below 1 micrometer diameter or %-submicron, for example. We denote the measured diameter (in μm) of an individual circular filament as di.

In case the filaments have non-circular cross-sections, the measurement of the filament diameter is determined as and set equal to the hydraulic diameter which is four times the cross-sectional area of the filament divided by the perimeter of the cross-section of the filament (outer perimeter in case of hollow filaments). The number-average diameter, alternatively average diameter is calculated as:

$$d_{num} = \frac{\sum_{i=1}^{n} d_i}{n}$$

Thickness Method

Thickness of a web (single or multi layer) is measured by cutting 5 samples of a web sample such that each cut sample is larger in size than a load foot loading surface of a VIR Electronic Thickness Tester Model II available from Thwing-Albert Instrument Company, Philadelphia, Pa. Typically, the load foot loading surface has a circular surface area of about 3.14 in$^2$. The sample is confined between a horizontal flat surface and the load foot loading surface. The load foot loading surface applies a confining pressure to the sample of 15.5 g/cm$^2$. The caliper of each sample is the resulting gap between the flat surface and the load foot loading surface. The caliper is calculated as the average caliper of the five samples. The result is reported in millimeters (mm).

Shear Viscosity Test Method

The shear viscosity of a filament-forming composition of the present invention is measured using a capillary rheometer, Goettfert Rheograph 6000, manufactured by Goettfert USA of Rock Hill S.C., USA. The measurements are conducted using a capillary die having a diameter D of 1.0 mm and a length L of 30 mm (i.e., L/D=30). The die is attached to the lower end of the rheometer's 20 mm barrel, which is held at a die test temperature of 75° C. A preheated to die test temperature, 60 g sample of the filament-forming composition is loaded into the barrel section of the rheometer. Rid the sample of any entrapped air. Push the sample from the barrel through the capillary die at a set of chosen rates 1,000-10, 000 seconds$^{-1}$. An apparent shear viscosity can be calculated with the rheometer's software from the pressure drop the sample experiences as it goes from the barrel through the capillary die and the flow rate of the sample through the capillary die. The log (apparent shear viscosity) can be plotted against log (shear rate) and the plot can be fitted by the power law, according to the formula $\eta=K\gamma^{n-1}$, wherein K is the material's viscosity constant, n is the material's thinning index and $\gamma$ is the shear rate. The reported apparent shear viscosity of the filament-forming composition herein is calculated from an interpolation to a shear rate of 3,000 sec$^{-1}$ using the power law relation.

Basis Weight Test Method

Basis weight of a single layer web is measured by selecting twelve (12) individual fibrous structure samples and making two stacks of six individual samples each. If the individual samples are connected to one another vie perforation lines, the perforation lines must be aligned on the same side when stacking the individual samples. A precision cutter is used to cut each stack into exactly 3.5 in.×3.5 in. squares. The two stacks of cut squares are combined to make a basis weight pad of twelve squares thick. The basis weight pad is then weighed on a top loading balance with a minimum resolution of 0.01 g. The top loading balance must be protected from air drafts and other disturbances using a draft shield. Weights are recorded when the readings on the top loading balance become constant. The Basis Weight is calculated as follows:

$$\text{Basis Weight (g/m}^2\text{)} = \frac{\text{Weight of basis weight single layer web }(g) \times 10{,}000 \text{ cm}^3/\text{m}^2}{79.0321 \text{ cm}^2 (\text{Area of basis weight pad}) \times 12 \text{ samples}}$$

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular examples and/or embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A razor cartridge comprising:
   a. a housing comprising a skin contacting surface;
   b. at least one blade having a blade tip; and
   c. a shaving aid positioned on said housing to expose a skin contacting portion of said shaving aid on said skin contacting surface, said shaving aid comprising at least one water soluble nano-filament having a diameter of from about 10 nm to about 1000 nm.

2. The razor cartridge of claim 1, wherein said at least one water soluble nano-filament has an average diameter of from about 300 nm to about 600 nm.

3. The razor cartridge of claim 1, wherein said shaving aid comprises at least 0.01% by weight of said at least one water soluble nano-filament.

4. The razor cartridge of claim 1, wherein said at least one water soluble nano-filament forms a nonwoven web.

5. The razor cartridge of claim 4, wherein said nonwoven web has a thickness of from about 0.01 mm to about 5 mm.

6. The razor cartridge of claim 1, wherein said at least one water soluble nano-filament has a span of at least 30 um between intersections with other nano-filaments when the shaving aid comprises more than one nano-filament.

7. The razor cartridge of claim 1, wherein at least a portion of said skin contacting portion has a surface coating, said surface coating comprising said at least one water soluble nano-filament.

8. The razor cartridge of claim 7, wherein at least 50% of the skin contacting portion, by surface area, is covered by said surface coating.

9. The razor cartridge of claim 7, wherein said surface coating comprises more than one layer.

10. The razor cartridge of claim 7, wherein said surface coating has a thickness of from about 0.01 mm to about 20 mm.

11. The razor cartridge of claim 1, further comprising a second nano-filament.

12. The razor cartridge of claim 11, wherein said second nano-filament is not water soluble.

13. The razor cartridge of claim 1, wherein said at least one water soluble nano-filament comprises filament forming material selected from the group consisting of polyvinyl alcohol, quaternary ammonium polymer, polyethylene glycol, polyethylene oxide, polypropylene oxide, and a combination thereof.

14. The razor cartridge of claim 13, wherein said at least one water soluble nano-filament comprises a copolymer of polyethylene oxide and polypropylene oxide.

15. The razor cartridge of claim 1, wherein said shaving aid comprises a plurality of nano-filaments, and wherein said plurality of nano-filaments are cross linked.

* * * * *